United States Patent [19]
Kahmann et al.

[11] Patent Number: 6,103,229
[45] Date of Patent: Aug. 15, 2000

[54] **REGULATOR GENE FROM *USTILAGO MAYDIS***

[75] Inventors: Regine Kahmann; Claudia Quadbeck-Seeger, both of München, Germany

[73] Assignee: BASF Aktiengesellschaft, Ludwigshafen, Germany

[21] Appl. No.: 09/051,019

[22] PCT Filed: Sep. 30, 1996

[86] PCT No.: PCT/EP96/04254

§ 371 Date: Mar. 31, 1998

§ 102(e) Date: Mar. 31, 1998

[87] PCT Pub. No.: WO97/12911

PCT Pub. Date: Apr. 10, 1997

[30] Foreign Application Priority Data

Oct. 4, 1995 [DE] Germany ............ 195 36 890
Mar. 25, 1996 [DE] Germany ............ 196 11 758

[51] Int. Cl.$^7$ .............. A01N 63/04; C12Q 1/68
[52] U.S. Cl. .............. 424/93.5; 426/627; 435/6; 536/23.74

[58] Field of Search ............ 514/44; 800/282; 536/24.1, 23.74; 530/350; 426/621, 627; 424/93.5; 435/6

[56] References Cited

FOREIGN PATENT DOCUMENTS

94/01459  1/1994  WIPO.

OTHER PUBLICATIONS

Banuett et al., *Proc. Natl. Acad. Sci.*, vol. 86, pp. 5878–5882, Aug. 1989.
Schauwecker et al., *Biol. Chem. Hoppe–Seyler*, vol. 376, pp. 617–625, Oct. 1995.
Barrett et al., *Molecular Plant–Microbe Interactions*, vol. 6, No. 3, pp. 274–283, 1993.
Schulz et al., *Cell*, vol. 60, pp. 295–306, Jan. 26, 1990.

*Primary Examiner*—James Ketter
*Attorney, Agent, or Firm*—Keil & Weinkauf

[57] ABSTRACT

The invention relates to a regulatory nucleic acid fragment from *Ustilago maydis* and to its use.

10 Claims, 9 Drawing Sheets

BglII
1 AGATCTACACTCTCTTTACGACCGTCTGTCAGTTAATGTTTCAAAGCCGAGCATCGTCCTGGATGCAGC
TCTAGATGTGAGAGAAATGCTGGCAGACAGTCAATTACAAAGTTTCGGCTCGTAGCAGGACCTACGTCG

70 TTGCTTTGCAGGCGTTAAAACCACATTTTTTCGATTTCGCTCTTCTCTATCAGTTGTTTCTTGATTATA
AACGAAACGTCCGCAATTTTGGTGTAAAAAAGCTAAAGCGAGAAGAGATAGTCAACAAAGAACTAATAT

139 TCTCGTGATACGTTGCATACCTTGTACACGGGTCGCAATTTAAGAGTTTCGTATTCATGACACTCGTGA
AGAGCACTATGCAACGTATGGAACATGTGCCCAGCGTTAAATTCTCAAAGCATAAGTACTGTGAGCACT

208 CTGATCTTGGCTTGCTCAAAGTTGGTCGTGCTCTGAAGACAGTGGCGATGCTAACAGACGATGCGGTAT
GACTAGAACCGAACGAGTTTCAACCAGCACGAGACTTCTGTCACCGCTACGATTGTCTGCTACGCCATA

277 ACAGGGAGACAAGGGTATGTCACGGTCGCTGGTTCGGAGATGTGTGAGCAGCAGGTGTGGACGCTAGCG
TGTCCCTCTGTTCCCATACAGTGCCAGCGACCAAGCCTCTACACACTCGTCGTCCACACCTGCGATCGC

346 ATTCAGAGGTCGAATGAGCTCCTTCGCAACAAGGCGAGGCAAAGCGTCCGTCAAGGCAGGGCATGCTGA
TAAGTCTCCAGCTTACTCGAGGAAGCGTTGTTCCGCTCCGTTTCGCAGGCAGTTCCGTCCCGTACGACT

415 TGAGGAGCTGCCACGCGAGTCGCGCCGACAGCGAAGCACACATGACGAGTCCCACGACACGGTCGTGGC
ACTCCTCGACGGTGCGCTCAGCGCGGCTGTCGCTTCGTGTGTACTGCTCAGGGTGCTGTGCCAGCACCG

484 CCGACGTCTACCACCGGTGCTGGTGTGTGCTGTAGGATGATTTGGACAGGGAGAGGAAGGCACACGACA
GGCTGCAGATGGTGGCCACGACCACACACGACATCCTACTAAACCTGTCCCTCTCCTTCCGTGTGCTGT

553 CGCGATCAGCTTGATAGCGAGCAACCCTTGTTCTGCTTGTTTTTGAACAGAGGGTGCTGTCATACGAGC
GCGCTAGTCGAACTATCGCTCGTTGGGAACAAGACGAACAAAAACTTGTCTCCCACGACAGTATGCTCG

622 GGCCAGACGCTGGCAATGGCCCACCGAATGTGATGGAGGAAAGCGCCATGGCAAGGCGCAGGCTCAGGA
CCGGTCTGCGACCGTTACCGGGTGGCTTACACTACCTCCTTTCGCGGTACCGTTCCGCGTCCGAGTCCT

691 ACGATAAGATGGTTTGATTCCCTATTCGACACACGAGTTGGCTATTAGTCGTGAGCGTGAGTCGTGAGT
TGCTATTCTACCAAACTAAGGGATAAGCTGTGTGCTCAACCGATAATCAGCACTCGCACTCAGCACTCA

760 GTGACTGGCGAAACACGACAGGTGCAGAGCTCGGCAACGAACTTTCGACTTGCGCCCACTTTACGCGGA
CACTGACCGCTTTGTGCTGTCCACGTCTCGAGCCGTTGCTTGAAAGCTGAACGCGGGTGAAATGCGCCT

829 GGAGCCGGGCGAGAGACAGCGAGGATGCTTGAAAAATAAAACAGGACAGGAATAACAACAAGTCGGCCA
CCTCGGCCCGCTCTCTGTCGCTCCTACGAACTTTTTATTTTGTCCTGTCCTTATTGTTGTTCAGCCGGT

898 TGCTTGACAGTCGGTGCATTTGCAGTGTGTCTAATTCTGCGAGGCATCACGCCTCCTGCCTTTTTTCCT
ACGAACTGTCAGCCACGTAAACGTCACACAGATTAAGACGCTCCGTAGTGCGGAGGACGGAAAAAAGGA

967 CCAAACCCACCCTTCCTGGCAGAAAGTGAGGCAGCAGAGAGAGGAAAAGAGAGAAAGAGTCACGAGTGG
GGTTTGGGTGGGAAGGACCGTCTTTCACTCCGTCGTCTCTCTCCTTTTCTCTCTTTCTCAGTGCTCACC

1036 GTGCCGCAATCACGAATATATTAATAATTCGAAACCAAAACGCTTTACAAGCATCAAGCACGAAGCTTA
CACGGCGTTAGTGCTTATATAATTATTAAGCTTTGGTTTTGCGAAATGTTCGTAGTTCGTGCTTCGAAT

1105 GGCCCTGCGTAATTCACGATTCACGATTCACGATTCACGATTGTGACTTGGAGCCAAGGCTGTGGCCTC
CCGGGACGCATTAAGTGCTAAGTGCTAAGTGCTAAGTGCTAACACTGAACCTCGGTTCCGACACCGGAG

1174 TGTCGCCTAACCCTTTTTTGACAGAGGCTTCTGAGCTTGAGCGTGGGTGCCACAAACTTGTCACGGCCT
ACAGCGGATTGGGAAAAAACTGTCTCCGAAGACTCGAACTCGCACCCACGGTGTTTGAACAGTGCCGGA

1243 CCGAAATCAGAGGTCCTCCTCATCATCTCAATTTTTTTTTGTGTTGGCGTGTCGTTCGCGCTAGCATCA
GGCTTTAGTCTCCAGGAGGAGTAGTAGAGTTAAAAAAAAAACACAACCGCACAGCAAGCGCGATCGTAGT

1312 AGACCATCACCACCATATCGATCACCGCGGCTGTGCTGCTGTCCGCCGCCCTGTCAGTACTGCTCCACG
TCTGGTAGTGGTGGTATAGCTAGTGGCGCCGACACGACGACAGGCGGCGGGACAGTCATGACGAGGTGC

1381 GTTCTCCTCAATCTCCGCCTCGCTGTTGTGTTTGTCTTCCACGGTGCTTCGCGCTCAGCTGCTGTGCTT
CAAGAGGAGTTAGAGGCGGAGCGACAACACAAACAGAAGGTGCCACGAAGCGCGAGTCGACGACACGAA

1450 TGATCACACATCGGGGTCGATTCCTAACTTGTGTAAGCGCCTTATCCCACCCAATTTGCCAAGTCGATA
ACTAGTGTGTAGCCCCAGCTAAGGATTGAACACATTCGCGGAATAGGGTGGGTTAAACGGTTCAGCTAT

1519 CCGCCGTTCTATCGCGGCTCTGGCCGGCGATTCTTGGCACTTTCCCAACAGTTGCCTTGTCGGACTAGC
GGCGGCAAGATAGCGCCGAGACCGGCCGCTAAGAACCGTGAAAGGGTTGTCAACGGAACAGCCTGATCG

1588 CGCAATCTTGGCTCACAACGTGCAAACTATCTGTCGAGATTCATGACGGCGCTTCCCTAGTCAGGATCG
GCGTTAGAACCGAGTGTTGCACGTTTGATAGACAGCTCTAAGTACTGCCGCGAAGGGATCAGTCCTAGC

1657 GAAAACGCCGCTCTCTCTGTGCCACATCGATTTCGCCTGCCACCAAAGGTGCACCTCTCTGTCTCTCCT
CTTTTGCGGCGAGAGAGACACGGTGTAGCTAAAGCGGACGGTGGTTTCCACGTGGAGAGACAGAGAGGA

1726 GAATACGTCCGCCGCTCATCTCAGCATCCTTCTCCTCCGTTCTATCTCCCTGCGCCTGCTGTTGTTCAT
CTTATGCAGGCGGCGAGTAGAGTCGTAGGAAGAGGAGCAAGATAGAGGGACGCGGACGACAACAAGTA

FIG. 3a

1795 CGATATCCGCCAGCATACGAGACACACGTTGGCAGCTCCTCGATCTCTAACCATGACATCCACCAAGAC
     GCTATAGGCGGTCGTATGCTCTGTGTGCAACCGTCGAGGAGCTAGAGATTGGTACTGTAGGTGGTTCTG

1864 AAGCTCTCAGCCCTCAGGCTCGAGTGACACTCCTCAACGCATCGTCGTCAAATCCGTCAATGGTCACGA
     TTCGAGAGTCGGGAGTCCGAGCTCACTGTGAGGAGTTGCGTAGCAGCAGTTTAGGCAGTTACCAGTGCT

1933 GCCCATCAAAGTAGAGCCTGTCTCCTCGTCCAGCGCATCACTGCTTCACTCCACACCGCCCCGGCTCGC
     CGGGTAGTTTCATCTCGGACAGAGGAGCAGGTCGCGTAGTGACGAAGTGAGGTGTGGCGGGGCCGAGCG

2002 CACACCGCTTTCCTCACCCACCAAATCAGCCGCCCCTCGAGTCCATCCAAGTCTCCAGGAAGGGCGCG
     GTGTGGCGAAAGGAGTGGGTGGTTTAGTCGGCGGGGGAGCTCAGGTAGGTTCAGAGGTCCTTCCCGCGC

2071 ACGTGTAGATCCTGTCTTGATCTCGTCTCGCGAGTTTGGCCCTAGTGCTGGAGGAGACAGCGATGACGA
     TGCACATCTAGGACAGAACTAGAGCAGAGCGCTCAAACCGGGATCACGACCTCCTCTGTCGCTACTGCT

2140 TGAGTTCAACAATGGCGAGCCCGAAGTTTACAAGGGCGTCAACACCACTGCCAAAAGGCTCAGCCGCAA
     ACTCAAGTTGTTACCGCTCGGGCTTCAAATGTTCCCGCAGTTGTGGTGACGGTTTTCCGAGTCGGCGTT

2209 GAGCAAGGCGGATGCTATGTTCGCCATGTCCGTCAAAGAGTCTTCTCCCGTCCATGCGCACGCAACATC
     CTCGTTCCGCCTACGATACAAGCGGTACAGGCAGTTTCTCAGAAGAGGGCAGGTACGCGTGCGTTGTAG

2278 CACATCTACCACTTCAAATGCTCCCACTGCCATCCCCGGCAACCCTGCCTCCCACCCAGCACGCAAAAT
     GTGTAGATGGTGAAGTTTACGAGGGTGACGGTAGGGCCGTTGGGACGGAGGGTGGGTCGTGCGTTTTA

2347 GTTCCAGCACCAGCCATTTCCGCCTCTGGTTTTCGATACAGATCCCATCTCATCCATCTCGCAGTCTCC
     CAAGGTCGTGGTCGGTAAAGGCGGAGACCAAAAGCTATGTCTAGGGTAGAGTAGGTAGAGCGTCAGAGG

2416 ATCCGCTTCCAATGCGGCTCAGCCCCCCATTCCAACTCATGCCAGCACGCCACGCTGCCCTCCGCCCAG
     TAGGCGAAGGTTACGCCGAGTCGGGGGGTAAGGTTGAGTACGGTCGTGCGGTGCGACGGGAGGCGGGTC

2485 GCTCCGTCCCAGACTCTTTGAGCTCGACGAAGCGCCCACTTTCTATCCATCGCCTGAAGAGTTCTCTGA
     CGAGGCAGGGTCTGAGAAACTCGAGCTGCTTCGCGGGTGAAAGATAGGTAGCGGACTTCTCAAGAGACT

2554 TCCAATGAAGTACATCGCCTGGATCGCCGACCCACAAGGTGGTAATGGCAAGGCATACGGCATCGTCAA
     AGGTTACTTCATGTAGCGGACCTAGCGGCTGGGTGTTCCACCATTACCGTTCCGTATGCCGTAGCAGTT

2623 GATCGTTCCACCTCAGGGCTGGAACCCGGAATGCGTGCTTGATGAGCAGACCTTCCGCTTTCGCACCCG
     CTAGCAAGGTGGAGTCCCGACCTTGGGCCTTACGCACGAACTACTCGTCTGGAAGGCGAAAGCGTGGGC

2692 CGTTCAGCTCCTCAACTCGCTCAGTGCAGATGCTCGGGCCTCTCAGAACTACCAGGAGCAACTGCAAAA
     GCAAGTCGAGGAGTTGAGCGAGTCACGTCTACGAGCCCGGAGAGTCTTGATGGTCCTCGTTGACGTTTT

2761 GTTCCACGCGCAGCAGGGTCGCAAGCGTGTCTCGGTCCCCGTCATTGACGGTCGTTCCGTCGATTTGTA
     CAAGGTGCGCGTCGTCCCAGCGTTCGCACAGAGCCAGGGGCAGTAACTGCCAGCAAGGCAGCTAAACAT

2830 CCAGCTCAAACTAGTCATCTCAAGTCTGGGTGGCTACGATGCTGTTTGCCGTGCTCGCAAGTGGTCCGA
     GGTCGAGTTTGATCAGTAGAGTTCAGACCCACCGATGCTACGACAAACGGCACGAGCGTTCACCAGGCT

2899 TGCTACGCGTAAGATCGGCTACAGTGACAAGGAAAGCGGTCAGCTCTCGACGCAAGTCAAAGCTGCCTA
     ACGATGCGCATTCTAGCCGATGTCACTGTTCCTTTCGCCAGTCGAGAGCTGCGTTCAGTTTCGACGGAT

2968 CACCCGCATCATCTTGCCCTTTGAAGAGTTTCTTGCAAAAGCAAAAGAGCAGTCTCGTCCTAACGGATC
     GTGGGCGTAGTAGAACGGGAAACTTCTCAAAGAACGTTTTCGTTTTCTCGTCAGAGCAGGATTGCCTAG

3037 ATCGGTCAGCCCACAGCTCGCGCAGAGTGCCATCATGGGCGCCACCGCCAGCACGGACACCCAAGAGAA
     TAGCCAGTCGGGTGTCGAGCGCGTCTCACGGTAGTACCCGCGGTGGCGGTCGTGCCTGTGGGTTCTCTT

3106 TGGCGTTAAGCACCCCTCCATGTCGCCAAGCCTCGACGCCGCCCCCAGTGGAGATGCAGGTGAACACTT
     ACCGCAATTCGTGGGGAGGTACAGCGGTTCGGAGCTGCGGCGGGGGTCACCTCTACGTCCACTTGTGAA

3175 CAAAACACCCGAGCCTTTCACTGCTGCTGGCGCTGCTGAGGCGCTCGCAAATGCAACTCCCGTCCTCGA
     GTTTTGTGGGCTCGGAAAGTGACGACGACCGCGACGACTCCGCGAGCGTTTACGTTGAGGGCAGGAGCT

3244 GACACCCACTCAAAGCCCTTCGACTGTCGCAAGCACACGTCGCAGTGCGCGCAAGAGATCGGAAGCAAC
     CTGTGGGTGAGTTTCGGGAAGCTGACAGCGTTCGTGTGCAGCGTCACGCGCGTTCTCTAGCCTTCGTTG

3313 CAGCACACCTGCTTCGTCGTCGCGTAACTCTTTGCAGCTCACCTCCACACCAATGACACCTTTGATCTC
     GTCGTGTGGACGAAGCAGCAGCGCATTGAGAAACGTCGAGTGGAGGTGTGGTTACTGTGGAAACTAGAG

3382 CAGACGCAGAAAGGGCGTTAGCCCTCACCTTGAAGCAGATTCTTACCTGCGCGCTCAAGCTGGCAATCA
     GTCTGCGTCTTTCCCGCAATCGGGAGTGGAACTTCGTCTAAGAATGGACGCGCGAGTTCGACCGTTAGT

3451 GGCGCAAGAAGAGCAAATGTGCGAAATCTGCCTCCGAGGCGAGGATGGTCCCAACATGTTGCTCTGCGA
     CCGCGTTCTTCTCGTTTACACGCTTTAGACGGAGGCTCCGCTCCTACCAGGGTTGTACAACGAGACGCT

3520 CGAGTGCAATCGTGGCTACCACATGTACTGTCTCCAACCCGCGCTCACTTCGATCCCCAAATCGCAGTG
     GCTCACGTTAGCACCGATGGTGTACATGACAGAGGTTGGGCGCGAGTGAAGCTAGGGGTTTAGCGTCAC

3589 GTTCTGCCCGCCTTGTCTTGTCGGCACCGGTCATGATTTTGGTTTTGACGATGGTGAAACACACAGCCT
     CAAGACGGGCGGAACAGAACAGCCGTGGCCAGTACTAAAAACCAAAACTGCTACCACTTTGTGTGTCGGA

FIG. 3b

```
3658 CTACACTTTTTGGCAACGTGCTGAGGCATTCAAGCGCGATTGGTGGTCCAAACATCAAGATCACCTCTG
     GATGTGAAAAACCGTTGCACGACTCCGTAAGTTCGCGCTAACCACCAGGTTTGTAGTTCTAGTGGAGAC
3727 GAGGCCCGACTCGGAAGGCCTGGCGACATCTGACTACGATCCGCCAACGAATGGTCTGGCTCGCCGTGT
     CTCCGGGCTGAGCCTTCCGGACCGCTGTAGACTGATGCTAGGCGGTTGCTTACCAGACCGAGCGGCACA
3796 CCACGGAACCGACCTGGTTGTGTCAGAGGACGACGTAGAGCGCGAATTTTGGAGACTAGTTCATAGCCA
     GGTGCCTTGGCTGGACCAACACAGTCTCCTGCTGCATCTCGCGCTTAAAACCTCTGATCAAGTATCGGT
3865 GAAGGAAGAAGTAGAAGTCGAGTATGGTGCTGACGTTCACTCTACTACGCACGGCAGTGCCTTGCCCAC
     CTTCCTTCTTCATCTTCAGCTCATACCACGACTGCAAGTGAGATGATGCGTGCCGTCACGGAACGGGTG
3934 CCAAGAGACTCATCCCTTGAGTCTGTATTCGCGCGACAAGTGGAACCTCAATAACCTACCCATCCTGCC
     GGTTCTCTGAGTAGGGAACTCAGACATAAGCGCGCTGTTCACCTTGGAGTTATTGGATGGGTAGGACGG
4003 TGGCTCGCTGCTCCAGTACATCAAGTCCGACATCTCGGGCATGACCGTCCCCTGGATCTATGTCGGAAT
     ACCGAGCGACGAGGTCATGTAGTTCAGGCTGTAGAGCCCGTACTGGCAGGGGACCTAGATACAGCCTTA
4072 GATTTTCTCCACCTTCTGCTGGCACAACGAGGATCACTACACTTACTCGATCAACTATCAGCATTGGGG
     CTAAAAGAGGTGGAAGACGACCGTGTTGCTCCTAGTGATGTGAATGAGCTAGTTGATAGTCGTAACCCC
4141 TGAGACTAAGACATGGTACGGCATTCCGGGTGAAGATGCCGAAAAGTTCGAGAATGCCATGCGCAAGGC
     ACTCTGATTCTGTACCATGCCGTAAGGCCCACTTCTACGGCTTTTCAAGCTCTTACGGTACGCGTTCCG
4210 GGCGCCCGATTTATTCGAGACGCTGCCGGACCTGCTCTTTCATCTCACCACCATGATGAGTCCCGAGAA
     CCGCGGGCTAAATAAGCTCTGCGACGGCCTGGACGAGAAAGTAGAGTGGTGGTACTACTCAGGGCTCTT
4279 GCTCAAGAAGGAAGGCGTCCGCGTTGTGGCATGTGACCAACGTGCCAACGAGTTTGTCGTCACTTTTCC
     CGAGTTCTTCCTTCCGCAGGCGCAACACCGTACACTGGTTGCACGGTTGCTCAAACAGCAGTGAAAAGG
4348 CAAGGCCTACCACAGCGGCTTTAACCACGGTCTCAACCTGAATGAAGCTGTCAACTTTGCTCTGCCCGA
     GTTCCGGATGGTGTCGCCGAAATTGGTGCCAGAGTTGGACTTACTTCGACAGTTGAAACGAGACGGGCT
4417 CTGGATCTTTGACGATCTCGAATCTGTTCGGAGGTACCAGCGCTTCCGAAAGCCTGCCGTATTCTCACA
     GACCTAGAAACTGCTAGAGCTTAGACAAGCCTCCATGGTCGCGAAGGCTTTCGGACGGCATAAGAGTGT
4486 CGACCAGCTGCTCATTACCGTCTCGCAGCAGAGTCAGACCATCGAAACAGCCGTGTGGCTTGAGGCCGC
     GCTGGTCGACGAGTAATGGCAGAGCGTCGTCTCAGTCTGGTAGCTTTGTCGGCACACCGAACTCCGGCG
4555 CATGCAAGAGATGGTTGATCGCGAGATCGCAAAGCGCAACGCACTTCGTGAGATCATTCCGGATCTCAA
     GTACGTTCTCTACCAACTAGCGCTCTAGCGTTTCGCGTTGCGTGAAGCACTCTAGTAAGGCCTAGAGTT
4624 AGAAGAGGTATACGACGAAGATGTAGCCGAGAGCCACTACATTTGCAGCCACTGCACTCTCTTTTCCTA
     TCTTCTCCATATGCTGCTTCTACATCGGCTCTCGGTGATGTAAACGTCGGTGACGTGAGAGAAAAGGAT
4693 CCTCGGCCAGTTGACAAGTCCAAAGACCGATGGTGTCGCTTGTCTCGATCACGGCTTCGAGGTGTGCAA
     GGAGCCGGTCAACTGTTCAGGTTTCTGGCTACCACAGCGAACAGAGCTAGTGCCGAAGCTCCACACGTT
4762 CGCCGATGCTCCCGTCAAGTGGACGTTGAAGCTTCGCTTCTCGGACGATCAGCTTCGCTCCATTCTAGC
     GCGGCTACGAGGGCAGTTCACCTGCAACTTCGAAGCGAAGAGCCTGCTAGTCGAAGCGAGGTAAGATCG
4831 GAAGGTCTGTGAGCGGGCAGCAGTGCCGCGCAACTGGATTCAGCGCCTCAAGAAGACCCTTGCTCTTGG
     CTTCCAGACACTCGCCCGTCGTCACGGCGCGTTGACCTAAGTCGCGGAGTTCTTCTGGGAACGAGAACC
4900 CCCGACTCCACCTCTCAAGACGCTGAGGTCGTTGCTGCACGAAGGCGAAAAGATTGCCTTCTCGCTAGA
     GGGCTGAGGTGGAGAGTTCTGCGACTCCAGCAACGACGTGCTTCCGCTTTTCTAACGGAAGAGCGATCT
4969 GCCGCTCGAGGATCTCAGGACCTTTGTCACCTGCGCCAACTCGTGGGTGGAGCGGGCCAATGTTTTCCT
     CGGCGAGCTCCTAGAGTCCTGGAAACAGTGGACGCGGTTGAGCACCCACCTCGCCCGGTTACAAAAGGA
5038 GATGCGCAAGTTGCATAAGAGACGCGGCGAGCCTGCAGCTGCTCCTGCTGGGAGGCGCCGACGATCCAA
     CTACGCGTTCAACGTATTCTCTGCGCCGCTCGGACGTCGACGAGGACGACCCTCCGCGGCTGCTAGGTT
5107 GGGCGGTGCTGTGGCTGACGATAGCTTCACTAGAAGGCAAAGCTTGGACGCTTCGGTCGACGATGCCGA
     CCCGCCACGACACCGACTGCTATCGAAGTGATCTTCCGTTTCGAACCTGCGAAGCCAGCTGCTACGGCT
5176 ATCCACTTCCGATCGAAGTCCCGAAGCCTTGTATGCGTTGATCGGAGAGCTCGACAGCCTTCACTTTGA
     TAGGTGAAGGCTAGCTTCAGGGCTTCGGAACATACGCAACTAGCCTCTCGAGCTGTCGGAAGTGAAACT
5245 CGCGCCTGAGATTGCATCGCTTCGCACTATGGCGCAAGAGCTCGAGGAGTTCATTGGCCGGTGTGACGA
     GCGCGGACTCTAACGTAGCGAAGCGTGATACCGCGTTCTCGAGCTCCTCAAGTAACCGGCCACACTGCT
5314 GGTCCTACAACAGGGTGACGAGACTAATCTCAAAGACTGTGAAAGCATCCTGACGCTCGGCAGCTCTCT
     CCAGGATGTTGTCCCACTGCTCTGATTAGAGTTTCTGACACTTTCGTAGGACTGCGAGCCGTCGAGAGA
                                                                    BamHI
5383 CAATGTGGACGCGCCTCAGATCAAAGAGCTCTCCGACTATGTCGAGCGTCGCAAGTGGATCCAGGAAGT
     GTTACACCTGCGCGGAGTCTAGTTTCTCGAGAGGCTGATACAGCTCGCAGCGTTCACCTAGGTCCTTCA
5452 CACAGAATCGTTCGACACATATCTCTATTACCACGAAGTTGCGGAACTGTTGGATCGCGCCGACAGCTG
     GTGTCTTAGCAAGCTGTGTATAGAGATAATGGTGCTTCAACGCCTTGACAACCTAGCGCGGCTGTCGAC
```

FIG. 3c

```
5521  TGGTCTACAAGATCACGAGCTGCGCAAGAATCTTGAGCAGAGACTCGAAGCCGGCCAACGCTGGACTGA
      ACCAGATGTTCTAGTGCTCGACGCGTTCTTAGAACTCGTCTCTGAGCTTCGGCCGGTTGCGACCTGACT
5590  AAGTGCAAGGGAAGCGCTGGGAGGCTCTCAGCCTATAACAATCGACGTGCTTCAAGAGCTTTCCGAGTC
      TTCACGTTCCCTTCGCGACCCTCCGAGAGTCGGATATTGTTAGCTGCACGAAGTTCTCGAAAGGCTCAG
5659  GTCAGCTGATGTTCCTGTTGTGCTCGAAGTGGCTCAGGATGTTACCGACGCTCTCTCCAAGGCCAAAGA
      CAGTCGACTACAAGGACAACACGAGCTTCACCGAGTCCTACAATGGCTGCGAGAGAGGTTCCGGTTTCT
5728  GCTGCAAAAGACCATCCAGACACTGTACAAGGCATTACAGACGGGAGCTCACGGCCATTCTGCAGCCGA
      CGACGTTTTCTGGTAGGTCTGTGACATGTTCCGTAATGTCTGCCCTCGAGTGCCGGTAAGACGTCGGCT
5797  TGCGGATGGTGACCTATCAATGATCTCGATCTCGGAAAATGGCGAAGCTGCCGAGCGTGTGGCTCTGCT
      ACGCCTACCACTGGATAGTTACTAGAGCTAGAGCCTTTTACCGCTTCGACGGCTCGCACACCGAGACGA
5866  TCCTGACGCTCGTCGCGTGCTTCGTGCCGCCAGGTCCAACAAACTGGAGCTTGAGCACGCGCAAGACAT
      AGGACTGCGAGCAGCGCACGAAGCACGGCGGTCCAGGTTGTTTGACCTCGAACTCGTGCGCGTTCTGTA
5935  TGAAAAGGCCGTCCAAGTCTACGATGCATGGCGAGCTGCGTTCAACCAGATCATGCAGACTATTGCCGG
      ACTTTTCCGGCAGGTTCAGATGCTACGTACCGCTCGACGCAAGTTGGTCTAGTACGTCTGATAACGGCC
6004  TGGATCTCGCCGCCTCACGGACGCAGACCGCGACGAGGAGCTCGACAAGCTGGTGGAGCGAGTCGAGGA
      ACCTAGAGCGGCGGAGTGCCTGCGTCTGGCGCTGCTCCTCGAGCTGTTCGACCACCTCGCTCAGCTCCT
6073  TGCCACCGACCCTGCCGACGACCAGAACAAACCCAATGCACGCAACTGTATCTGCAGGAGCTCAATGCC
      ACGGTGGCTGGGACGGCTGCTGGTCTTGTTTGGGTTACGTGCGTTGACATAGACGTCCTCGAGTTACGG
6142  CATCGCCATTCCTTCGTCGTCAGGGGCAGAATGCTCTCGCTGTCGCGTGCAGTACCATCTATCGTGCAT
      GTAGCGGTAAGGAAGCAGCAGTCCCGTCTTACGAGAGCGACAGCGCACGTCATGGTAGATAGCACGTA
6211  CAAGGTGCGCTCCTCTGAGGTATCACGCGCCGAGGGCGGCTGGGTTTGTCCATTCTGCCCGTGGTACGG
      GTTCCACGCGAGGAGACTCCATAGTGCGCGGCTCCCGCCGACCCAAACAGGTAAGACGGGCACCATGCC
6280  GAGCGCTCCGTTCCTCAAAATGCGCAAGGCGATCAGCATTGCTGACCTTTCGAAGCTTGTATACGATCA
      CTCGCGAGGCAAGGAGTTTTACGCGTTCCGCTAGTCGTAACGACTGGAAAGCTTCGAACATATGCTAGT
6349  AGATCATCGTCGAGACCAGTTCAAATTCCTCCCTCTGGAATGGGACGCCATCGAGGAAGTGGTTGCCAA
      TCTAGTAGCAGCTCTGGTCAAGTTTAAGGAGGGAGACCTTACCCTGCGGTAGCTCCTTCACCAACGGTT
6418  GGCAAAGCGATTCGAGACGGCCGCTAAGCGAATGATCAAAACACTTTCGCTGATGCGCAGAGATCAAAA
      CCGTTTCGCTAAGCTCTGCCGGCGATTCGCTTACTAGTTTTGTGAAAGCGACTACGCGTCTCTAGTTTT
6487  GCAGGTCATCCTTGCCCACTGGCTACGTCGGTCCATTGGCTGCCCCGTCGATGTCTTGGGACCAGAGAA
      CGTCCAGTAGGAACGGGTGACCGATGCAGCCAGGTAACCGACGGGGCAGCTACAGAACCCTGGTCTCTT
6556  AGTCAACATGCTTGACCTCATCAGCGAAAATTTGCTCGCCCTTGGTTCACAGCAGGGTGATGCTGCACC
      TCAGTTGTACGAACTGGAGTAGTCGCTTTTAAACGAGCGGGAACCAAGTGTCGTCCCACTACGACGTGG
6625  CATGGCGCCTGTTGAGCGTATCAAGGCGTCGACTCCAGCGCGATCCGACGAGCGCACGGAAGAAACAAC
      GTACCGCGGACAACTCGCATAGTTCCGCAGCTGAGGTCGCGCTAGGCTGCTCGCGTGCCTTCTTTGTTG
6694  GCCCTTGCCTCGCTCGTCTCGCGTTCCAGCCCCTGCCGATCGCGACTCAGGATCTCCAGCTGTCCGAGA
      CGGGAACGGAGCGAGCAGAGCGCAAGGTCGGGGACGGCTAGCGCTGAGTCCTAGAGGTCGACAGGCTCT
6763  CGATCGCAAGCGCAAAGCCAAGAGAGGCAAGCGTGCCAAGCTCGTCTTCCAGGAGGAGATTGGTATCGG
      GCTAGCGTTCGCGTTTCGGTTCTCTCCGTTCGCACGGTTCGAGCAGAAGGTCCTCCTCTAACCATAGCC
6832  TGCTTACCGCGATCGTCAGCCCATCTACTGTCTGTGCCATGAGCCAGAGAGCGGTCGCATGATTGCTTG
      ACGAATGGCGCTAGCAGTCGGGTAGATGACAGACACGGTACTCGGTCTCTCGCCAGCGTACTAACGAAC
6901  TGACAAGTGCATGCTCTGGTTTCATACCAATTGTGTTCGCCTCGATGATCCGCCGAATCTCGGAAATGA
      ACTGTTCACGTACGAGACCAAAGTATGGTTAACACAAGCGGAGCTACTAGGCGGCTTAGAGCCTTTACT
6970  GCCGTGGATATGTCCCATGTGCTGCATCAAGGCGGAGCGCAAGTATCCTCAGGCCGAAGTCAGGGTCAA
      CGGCACCTATACAGGGTACACGACGTAGTTCCGCCTCGCGTTCATAGGAGTCCGGCTTCAGTCCCAGTT
7039  AGACATTGGCGTCACCGACCCGGATCTGTGGCTCGACATCCGTGCCACGCTGCGATCGCTCGAGAAGCC
      TCTGTAACCGCAGTGGCTGGGCCTAGACACCGAGCTGTAGGCACGGTGCGACGCTAGCGAGCTCTTCGG
7108  TGTCAGCAAGATTCAGTCGTGGACCAGCCCGGAGAACAAGCGCATTGTGCTACATCTGGAAAAGTTCAC
      ACAGTCGTTCTAAGTCAGCACCTGGTCGGGCCTCTTGTTCGCGTAACACGATGTAGACCTTTTCAAGTG
7177  ACCGGCTATCCATGCTGAGGAGGTGCACTCGCAGATCACCAAACGTGCGCGTCTCGAGTCCGACACGCC
      TGGCCGATAGGTACGACTCCTCCACGTGAGCGTCTAGTGGTTTGCACGCGCAGAGCTCAGGCTGTGCGG
7246  GAGCAAGGCGCGAGTGTCTCTGGGCCGCTCTGATTCGATCTCGACGCCAGCAAAGGAGAGCGGCGCCGT
      CTCGTTCCGCGCTCACAGAGACCCGGCGAGACTAAGCTAGAGCTGCGGTCGTTTCCTCTCGCCGCGGCA
7315  TCCTTATGCGGCAGCTCCTGTGCCCAGCGAGGCTGTTCGAGGTATCGTGCCTGCTTTGACGCCGGCGGC
      AGGAATACGCCGTCGAGGACACGGGTCGCTCCGACAAGCTCCATAGCACGGACGAAACTGCGGCCGCCG
```

FIG. 3d

```
7384  TGATTCACCCGCCTCCAGATCAGGAAGGAACGACGATTCATTTGCTGCAGCCTCGCCTCCTTTGTGGGA
      ACTAAGTGGGCGGAGGTCTAGTCCTTCCTTGCTGCTAAGTAAACGACGTCGGAGCGGAGGAAACACCCT

7453  TGCCAAGACTGGACCATCTCCTGGCAACGCCAGCATCGAATGGGCGCAGTCGGCACGTCGACGATATGC
      ACGGTTCTGACCTGGTAGAGGACCGTTGCGGTCGTAGCTTACCCGCGTCAGCCGTGCAGCTGCTATACG

7522  CGAAGGCATGGACAACCTCTACCGTCGCGGCATCACGGACACGATGCTGGTGCGATTCTACGTTGGATG
      GCTTCCGTACCTGTTGGAGATGGCAGCGCCGTAGTGCCTGTGCTACGACCACGCTAAGATGCAACCTAC

7591  GAATGGACGTACGCTCTTTCATCCGGTACGAGACTCAGCGGGCAACATTGTAGAGGTATCTCTGGGCGA
      CTTACCTGCATGCGAGAAAGTAGGCCATGCTCTGAGTCGCCCGTTGTAACATCTCCATAGAGACCCGCT

7660  GAACGTCCGTCTGCATCCAGATGATCCCGAGGGCGTGCGGGTAATTCGTGCTGCCATTGAACGACACAG
      CTTGCAGGCAGACGTAGGTCTACTAGGGCTCCCGCACGCCCATTAAGCACGACGGTAACTTGCTGTGTC

7729  CGTCAAAGCGGACCGTTTAGCCGCAAGTCATGGCTATGGCGGCGAGATGGACGATCATGTGTACTCTCG
      GCAGTTTCGCCTGGCAAATCGGCGTTCAGTACCGATACCGCCGCTCTACCTGCTAGTACACATGAGAGC

7798  CAACGCTTACAGTCGCGACGACGGACGCTATACAGCTCAGCGACGCGATCCTCCGGTGGTACCGTCGAA
      GTTGCGAATGTCAGCGCTGCTGCCTGCGATATGTCGAGTCGCTGCGCTAGGAGGCCACCATGGCAGCTT

7867  TGGCAGATTCAGCATGAGATCGCCTGCCACGATTCCTTCGCAACGACTTGGCAGCGATCGCGACTATGA
      ACCGTCTAAGTCGTACTCTAGCGGACGGTGCTAAGGAAGCGTTGCTGAACCGTCGCTAGCGCTGATACT

7936  ACGCGAGCGGGAGCGTGACGGGGATCTTCATGATGCCCGTGATGGTCGTGATGGCCGATATGGCGATTC
      TGCGCTCGCCCTCGCACTGCCCCTAGAAGTACTACGGGCACTACCAGCACTACCGGCTATACCGCTAAG

8005  ATTACGTTCTCCGGCGGCACCAGTGGCGGCGATGACTGCCCCTGGTGCATTGGACACCTCGCCGGCGCT
      TAATGCAAGAGGCCGCCGTGGTCACCGCCGCTACTGACGGGGACCACGTAACCTGTGGAGCGGCCGCGA

8074  CCGAACGAATCTAGCGCGCGAAGTCGTGCCGACATACGCGCGAAGCTCAGCTAATGCATCGGCAACCAC
      GGCTTGCTTAGATCGCGCGCTTCAGCACGGCTGTATGCGCGCTTCGAGTCGATTACGTAGCCGTTGGTG

8143  AAGTCCATACACTGGCGCTGCTTCGACGTACAGCATTTATTCGGCATCTGACAGAGCGGCATCTTATCC
      TTCAGGTATGTGACCGCGACGAAGCTGCATGTCGTAAATAAGCCGTAGACTGTCTCGCCGTAGAATAGG

8212  GGTGGGTCGCAGTTCGATTTCGCAGGCGGATCTGGATGGAAATAGGGGGGGACCTCCACCGATGGCGAT
      CCACCCAGCGTCAAGCTAAAGCGTCCGCCTAGACCTACCTTTATCCCCCCCTGGAGGTGGCTACCGCTA

8281  GTATGCTTCTGCCAAGGCTGAGCCTGTCGCAAATGGGTCTACGTTTTCGGCACTGGACCCAGCGATGAT
      CATACGAAGACGGTTCCGACTCGGACAGCGTTTACCCAGATGCAAAAGCCGTGACCTGGGTCGCTACTA

8350  GGCAGACGATGCAGCAGGACAGATCGATCCCAATTTGACGAGCAGTCCGGTTCTAGCTTCCAACTCGGC
      CCGTCTGCTACGTCGTCCTGTCTAGCTAGGGTTAAACTGCTCGTCAGGCCAAGATCGAAGGTTGAGCCG

8419  AGTTCCCGCACCGTCGACCGCACCGGCAGCAGCACATGGTGTTCGGAGCGAGACGAGGAGCCGTCCACC
      TCAAGGGCGTGGCAGCTGGCGTGGCCGTCGTCGTGTACCACAAGCCTCGCTCTGCTCCTCGGCAGGTGG

8488  CAGCGCAGGCAACGAAGTCGCCCATGAAGCCGGTTCCGCGAAAGCACCCCGGGTGCACCCTCGGGTGG
      GTCGCGTCCGTTGCTTCAGCGGGTACTTCGGCCAAGGCGCTTTCGTGGGGGCCCACGTGGGAGCCCACC

8557  CCACAGTGGCGAGATCAAGGAGCACAACCCAGACGAGCACGAGCTCGAGAGTGTTCGTCAGCAGGCTAG
      GGTGTCACCGCTCTAGTTCCTCGTGTTGGGTCTGCTCGTGCTCGAGCTCTCACAAGCAGTCGTCCGATC

8626  ACAGATGGCGCGGAAAATGCGACCAGACGCTTCCGAGGCCGACATCGAACGATTGGTTCAAAACTTTAT
      TGTCTACCGCGCCTTTTACGCTGGTCTGCGAAGGCTCCGGCTGTAGCTTGCTAACCAAGTTTTGAAATA

8695  CGGTGGTGGAGAGTCTAAGTAGCGCGCCCTGCCAAGAATACATGCGGTTCAATGAAATTGTGAATCAAG
      GCCACCACCTCTCAGATTCATCGCGCGGGACGGTTCTTATGTACGCCAAGTTACTTTAACACTTAGTTC

8764  AATCATGAATCGTGAATGTACAATCGATATCACACCACGCAGCACGAATAGCGAGATTCACGATTCACG
      TTAGTACTTAGCACTTACATGTTAGCTATAGTGTGGTGCGTCGTGCTTATCGCTCTAAGTGCTAAGTGC

8833  AATCGTGATTCGTGAATCACGAATGTGCGAACGAAAATCAGGGTTTGGATTCCAAGAGAAAGAAGCTGA
      TTAGCACTAAGCACTTAGTGCTTACACGCTTGCTTTTAGTCCCAAACCTAAGGTTCTCTTTCTTCGACT

XbaI
8902  TGAAACAGTGATGAGTCAAACGAGTCTAGA
      ACTTTGTCACTACTCAGTTTGCTCAGATCT
```

FIG. 3e

```
          10         20         30         40         50         60
MTSTKTSSQPSGSSDTPQRIVVKSVNGHEPIKVEPVSSSSASLLHSTPPRLATPLSSPTK    60
SAAPSSPSKSPGRARRVDPVLISSREFGPSAGGDSDDDEFNNGEPEVYKGVNTTAKRLSR   120
KSKADAMFAMSVKESSPVHAHATSTSTTSNAPTAIPGNPASHPARKMFQHQPFPPLVFDT   180
DPISSISQSPSASNAAQPPIPTHASTPRCPPPRLRPRLFELDEAPTFYPSPEEFSDPMKY   240
IAWIADPQGGNGKAYGIVKIVPPQGWNPECVLDEQTFRFRTRVQLLNSLSADARASQNYQ   300
         310        320        330        340        350        360
EQLQKFHAQQGRKRVSVPVIDGRSVDLYQLKLVISSLGGYDAVCRARKWSDATRKIGYSD   360
KESGQLSTQVKAAYTRIILPFEEFLAKAKEQSRPNGSSVSPQLAQSAIMGATASTDTQEN   420
GVKHPSMSPSLDAAPSGDAGEHFKTPEPFTAAGAAEALANATPVLETPTQSPSTVASTRR   480
SARKRSEATSTPASSSRNSLQLTSTPMTPLISRRRKGVSPHLEADSYLRAQAGNQAQEEQ   540
MCEICLRGEDGPNMLLCDECNRGYHMYCLQPALTSIPKSQWFCPPCLVGTGHDFGFDDGE   600
         610        620        630        640        650        660
THSLYTFWQRAEAFKRDWWSKHQDHLWRPDSEGLATSDYDPPTNGLARRVHGTDLVVSED   660
DVEREFWRLVHSQKEEVEVEYGADVHSTTHGSALPTQETHPLSLYSRDKWNLNNLPILPG   720
SLLQYIKSDISGMTVPWIYVGMIFSTFCWHNEDHYTYSINYQHWGETKTWYGIPGEDAEK   780
FENAMRKAAPDLFETLPDLLFHLTTMMSPEKLKKEGVRVVACDQRANEFVVTFPKAYHSG   840
FNHGLNLNEAVNFALPDWIFDDLESVRRYQRFRKPAVFSHDQLLITVSQQSQTIETAVWL   900
         910        920        930        940        950        960
EAAMQEMVDREIAKRNALREIIPDLKEEVYDEDVAESHYICSHCTLFSYLGQLTSPKTDG   960
VACLDHGFEVCNADAPVKWTLKLRFSDDQLRSILAKVCERAAVPRNWIQRLKKTLALGPT  1020
PPLKTLRSLLHEGEKIAFSLEPLEDLRTFVTCANSWVERANVFLMRKLHKRRGEPAAAPA  1080
GRRRRSKGGAVADDSFTRRQSLDASVDDAESTSDRSPEALYALIGELDSLHFDAPEIASL  1140
RTMAQELEEFIGRCDEVLQQGDETNLKDCESILTLGSSLNVDAPQIKELSDYVERRKWIQ  1200
        1210       1220       1230       1240       1250       1260
EVTESFDTYLYYHEVAELLDRADSCGLQDHELRKNLEQRLEAGQRWTESAREALGGSQPI  1260
TIDVLQELSESSADVPVVLEVAQDVTDALSKAKELQKTIQTLYKALQTGAHGHSAADADG  1320
DLSMISISENGEAAAERVALLPDARRVLRAARSNKLELEHAQDIEKAVQVYDAWRAAFNQI  1380
MQTIAGGSRRLTDADRDEELDKLVERVEDATDPADDQNKPNARNCICRSSMPIAIPSSSG  1440
AECSRCRYQYHLSCIKVRSSEVSRAEGGWVCPFCPWYGSAPFLKMRKAISIADLSKLVYD  1500
        1510       1520       1530       1540       1550       1560
QDHRRDQFKFLPLEWDAIEEVVAKAKRFETAAKRMIKTLSLMRRDQKQVILAHWLRRSIG  1560
CPVDVLGPEKVNMLDLISENLLALGSQQGDAAPMAPVERIKASTPARSDERTEETTPLPR  1620
SSRVPAPADRDSGSPAVRDDRKRKAKRGKRAKLVFQEEIGIGAYRDRQPIYCLCHEPESG  1680
RMIACDKCMLWFHTNCVRLDDPPNLGNEPWICPMCCIKAERKYPQAEVRVKDIGVTDPDL  1740
WLDIRATLRSLEKPVSKIQSWTSPENKRIVLHLEKFTPAIHAEEVHSQITKRARLESDTP  1800
        1810       1820       1830       1840       1850       1860
SKARVSLGRSDSISTPAKESGAVPYAAAPVPSEAVRGIVPALTPAADSPASRSGRNDDSF  1860
AAASPPLWDAKTGPSPGNASIEWAQSARRRYAEGMDNLYRRGITDTMLVRFYVGWNGRTL  1920
FHPVRDSAGNIVEVSLGENVRLHPDDPEGVRVIRAAIERHSVKADRLAASHGYGGEMDDH  1980
VYSRNAYSRDDGRYTAQRRDPPVVPSNGRFSMRSPATIPSQRLGSDRDYERERERDGDLH  2040
DARDGRDGRYGDSLRSPAAPVAAMTAPGALDTSPALRTNLAREVVPTYARSSANASATTS  2100
```

FIG. 4a

```
          2110      2120      2130      2140      2150      2160
PYTGAASTYSIYSASDRAASYPVGRSSISQADLDGNRGGPPPMAMYASAKAEPVANGSTF 2160
SALDPAMMADDAAGQIDPNLTSSPYLASNSAVPAPSTAPAAAHGVRSETRSRPPSAGNEV 2220
AHEAGSAKAPPGAPSGGHSGEIKEHNPDEHELESVRQQARQMARKMRPDASEADIERLVQ 2280
NFIGGGESK. 2290
```

FIG. 4b

REGULATOR GENE FROM *USTILAGO MAYDIS*

The present invention relates to a regulatory gene from the fungus *Ustilago maydis*, to the use of this gene, and to fungal mutants which harbor a mutation in this gene.

*Ustilago maydis*, the organism causing blister smut of corn, has a two-phase life cycle. The haploid stage grows like a yeast and is not pathogenic. The dikaryon shows filamentous growth and represents the pathogenic form. The fungus has two mating type loci. The a locus, of which two alleles exist, is responsible for the fusion of haploid cells and the formation of the dikaryon. The multiallelic b locus controls the pathogenicity and the sexual development of the fungus. It codes for two homeodomain proteins (bW and bE) which form functional heterodimers.

A b locus-regulated gene egl1 codes for an endoglucanase whose expression is induced in the filamentous phase. Expression of the glucanase egl1 can be detected reliably and unambiguously using indicator plates based on carboxymethylcellulose with congo red. Hence egl1 is suitable as reporter gene for searching for genes with regulatory functions for the expression of differentially expressed genes. Since the filamentous phase of *Ustilago maydis* is pathogenic for corn, the object was to identify genes or gene products linked to the regulation of the filamentous phase. Such genes or gene products ought to represent suitable possibilities for intervention to eliminate the pathogenicity.

We have now found a nucleic acid fragment from the fungus *Ustilago maydis* which contains a regulatory gene.

The invention relates to a nucleic acid fragment from the fungus *Ustilago maydis* which comprises the XbaI-BglII fragment depicted in FIG. 1 and which comprises the nucleic acid sequence indicated in FIG. 3 between the BglII and the XbaI cleavage site.

BRIEF DESCRIPTION OF THE FIGURES

FIG. 3 depicts the sequence of the nucleic acid fragment from the fungus *Ustilago maydis* between the XbaI and BglII cleavage sites.

FIG. 4 depicts the amino acid sequence of the gene product of the nucleic acid fragment of FIG. 3.

Figure 1:
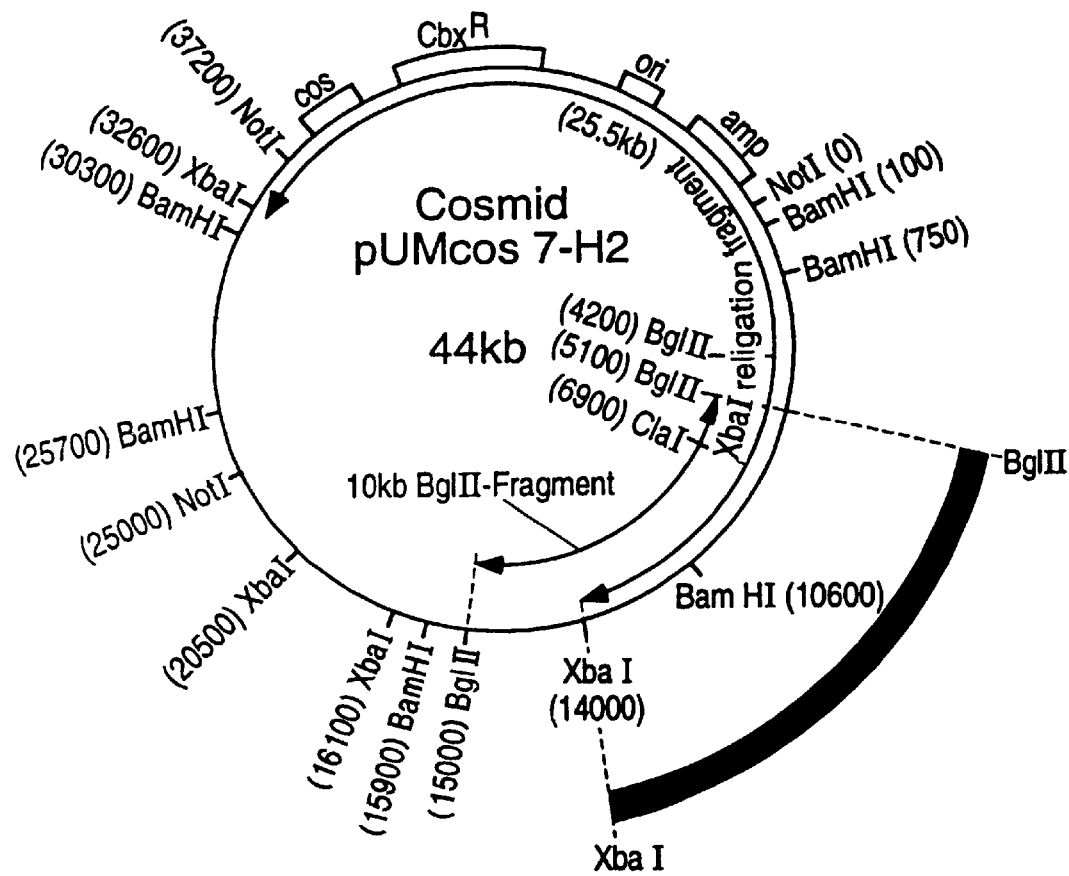
FIG. 1 depicts a nucleic acid fragment from the fungus *Ustilago maydis* which comprises the XbaI-BglII fragment.

The nucleic acid fragment was isolated in the following way:

A haploid *Ustilago maydis* strain FB1 (a1 b1) (Banuett, F. and Herskowitz, I. (1989), Different a alleles of *Ustilago maydis* are necessary for maintenance of filamentous growth but not for meiosis, Proc. Acad. Sci. U.S.A. 86: 5878–5882), which does not express the endoglucanase egl1 was subjected to UV mutagenesis. Screening of the resulting mutants for constitutive egl1 expression on carboxymethylcellulose plates followed by congo red staining revealed one mutant with the property which was sought, ie. filament-independent constitutive egl1 expression.

Detailed investigation of the resulting mutant revealed that other, normally differentially expressed, genes were expressed constitutively in this mutant. The gene affected by the mutation was further characterized by carrying out a complementation analysis (as described in detail in Example 3).

Analysis of the nucleic acid fragment revealed that the regulatory gene in this case presumably has a repressing action. This regulatory gene or the relevant gene product thus represents a possible specific site of action for fungicides. It is easily possible in a test method to test possible fungicidal compounds for interaction with the site of action which has been found, by bringing a haploid Ustilago strain which does not express endoglucinase egl1 in contact with the potential fungicide and determining whether egl1 expression takes place. In the positive case it is possible to assume interaction of the fungicide with the regulatory gene product.

A test method of this type can be carried out particularly straightforwardly if the screening for egl1 expression is done using carboxymethylcellulose plates, which are stained with congo red.

The invention furthermore relates to homologous nucleic acid fragments from other microorganisms which are likewise capable of functional complementation of a constitutively expressing *Ustilago maydis* mutant. Nucleic acid fragments of this type can easily be prepared by conventional methods of genetic engineering such as hybridization, by starting from the Ustilago nucleic acid fragment as probe and isolating and functionally testing appropriate clones, which hybridize under standard conditions, from other organisms.

The invention further relates to a) a gene product of the above-defined nucleic acid fragment which is represented by the amino acid sequence depicted in FIG. 4 (SEQ ID No:2) and is encoded in particular by the nucleic acid sequence shown in FIG. 3, by the open reading frame starting with the ATG start codon of position 1847–1849 and ending with the TAG stop codon in position 8714–8716;

b) the use of the gene product as depicted in FIG. 4 or of part-sequences derived therefrom as target for fungicides.

EXAMPLE 1

UV Mutation of the *Ustilago maydis* Strain FB1

The strain was inoculated in YEPS liquid medium (Tsukuda, T., S., Fotheringham, S. and Holloman, W. K. (1988), Isolation and characterization of an autonomously replicating sequence from *Ustilago maydis*. Mol. Cell. Biol. 8: 3703–3709) and shaken at 28° C. The cultures were centrifuged at a cell count of $1 \times 10^6$ to $3 \times 10^6$ and resuspended in the same amount of double-distilled $H_2O$. 1 ml of this cell suspension was treated with UV in a Petri dish. The irradiation times were chosen so that the survival rates were below 1%. Aliquots of the UV-treated cell suspension were then plated out.

The screening for mutants took place on carboxymethylcellulose plates (0.5% yeast extract, 0.4% Bacto peptone, 0.4% sucrose, 2% carboxymethylcellulose, 1.5% Bitek agar).

The colonies from the UV mutagenesis were replica plated on the test plates or, if the colony densities were too high, picked out and transferred, and incubated at 29° C. The cells were then washed off the plates for the test for egl1 expression. The plates were subsequently covered with 1% congo red for 20 minutes and decolorized with 1 M NaCl. The expression of egl1 is revealed by a pale halo.

EXAMPLE 2

Characterization of the Resulting Mutant

The mutant was crossed with a compatible wild-type strain (FB2 a2b2, Banuett and Herskowitz, 1989) in: Handbook of Genetics, Vol 1, R. C. King, ed. (New York: Plenum Press), pp. 575–595) on CM charcoal plates (Holliday, R. (1974) in order to eliminate mutations in the b locus. It emerged from this that the mutant chose the same crossing behavior as the starting strain.

RNA was prepared from liquid cultures of the mutant in YEPS (Schmitt, M. E., Brown, T. A., and Trumpower, B. L. (1990). A rapid and simple method for preparation of RNA from *Saccharomyces cerevisiae*. Nucl. Acid Res. 18, 3091–3092) and Northern analyses were carried out. Standard methods for blotting RNA onto nylon filters (Pall) were used (Sambrook J., Fritsch, E. F. and Maniatis, T. (1989). Molecular Cloning: A Laboratory Manual (Cold Spring Harbor, N.Y.: Cold Spring Harbor Laboratory Press).

The probe used for the Northern blots was a HindIII-SacI fragment from the open reading frame of the egl1 gene (dissertation of Florian Schauwecker "Isolierung und Charakterisierung einer filamentspezifischen exprimierten Cellulase aus *Ustilago maydis*", Free University Berlin, 1995).

DNA was radiolabeled with $^{32}$P using the Megaprime® labeling kit (Amersham). It was shown that egl1 is expressed in the mutant. The expression of other differentially expressed genes was also detectable in the mutant.

The resulting mutant is not pathogenic in the haploid state. When it is crossed with a compatible wild-type strain, infection of corn plants is followed by tumor formation and the formation of basidiospores. It was possible to isolate a compatible strain which resulted after segregation, and likewise harbors the mutation, from the spores from such a cross. Although crossing of this strain with the originally obtained mutant leads to tumor formation in the plant, spores are no longer formed with this cross.

A mutated Ustilago strain produced in this way can be used, for example, to induce the formation of tumors (galls) in corn plants without the black discoloration by spores.

Since the galls of the corn plants are used as food in some cases, infection with the described Ustilago mutant has the advantage, compared with the wild type, that the resulting galls are visually more attractive.

EXAMPLE 3

Complementation of the Mutant with an Ustilago Cosmid Bank

The mutant was complemented with a cosmid bank which had been prepared from genomic DNA of the diploid strain FBD11 (a1a2b1b2) (Banuett and Herskowitz, 1989, see above). To do this, partially cut MboI fragments were cloned into Bam HI cleavage sites of the cosmid vector pUMcos. puMcos is a modified pScos 1 vector (Stratagene; Wahl, G. M., Lewis, K. S., Ruiz, J. C., Rothenberg, B. Zhao, J., Evans, G. A. (1987) Cosmid vectors for rapid genomic walking, restriction mapping, and gene transfer Proc. Natl. Acad. Sci. U.S.A. 84: 2160–2164). In pScos, a HindIII-SmaI fragment of the neomycin resistance gene has been replaced by an EcoRV-SmaI fragment which confers carboxin resistance in *U. maydis* (indicated by cbxR in FIG. 1).

The EcoRV-SmaI fragment is derived from pCBX122 (Keon, J. P. R., White, G. A., Hargreaves, J. A. (1991), Isolation, characterization and sequence of a gene conferring resistance to the systemic fungicide carboxin from the maize smut pathogen, *Ustilago maydis*. Curr. Genet. 19: 475–481).

The mutant was transformed with the cosmid bank. Transformation of *U. maydis* by the method of Schulz, B., Banuett, F., Dahl, M., Schlesinger, R., Schäfer, W., Martin, T., Herskowitz, I. and Kahmann, R. (1990) (The b alleles of *U. maydis*, whose combinations program pathogenic development, code for polypeptides containing a homeodomain-related motif. Cell 60: 295–306). Pools of 98 cosmids were transformed.

Screening for complemented transformants took place on carboxymethylcellulose plates. It was possible to identify one complemented transformant. Chromosomal DNA was isolated from a YEPS liquid culture of this strain by the method of Hoffman, S. S. and Winston, F. (1987) (A ten-minute DNA preparation from yeast efficiently releases autonomous plasmids for transformation of *Escherichia coli*. Gene 57: 267–272). 1 µg of DNA was cut with SalI and religated in a volume of 20 µl. The ligation mixture was transformed into *E. coli* DH5a. Transformation was carried out using a Biorad electroporation unit in accordance with the manufacturer's protocol. The plasmids were isolated from the transformants by a boiling miniprep (Sambrook, J., Fritsch, E. F. and Maniatis, T. (1989). Molecular Cloning: A Laboratory Manual (Cold Spring Harbor, N.Y.: Cold Spring Harbor Laboratory Press).

Digestion with EcoRI and SalI resulted in a fragment from the rescue plasmid which consists of *U. maydis* DNA. This was radiolabelled and used to screen the individual filters of the cosmid pool with which complementation was possible. The hybridization was carried out at 65° C.

The cosmid pUMcos7-H2 (see FIG. 1), which had been identified in this way, was transformed anew into the mutant. It was possible in this way to confirm the complementation.

EXAMPLE 4

Characterization of the Complementing Nucleic Acid Fragment

Restriction analysis of the cosmid was carried out. The cosmid was digested with BamHI, and the fragments were fractionated and isolated on a 0.8% agarose gel. The fragments were cloned into the integrative vector pHLN4. pHLN4 is derived from pHL1 (Wang, J., Holden, D. W., and Leong, S. A. (1988). Gene transfer system for the phytopathogenic fungus *U. maydis*, Proc. Natl. Acad. Sci. U.S.A. 85, 865–869). pHL1 is a pUC12 derivative which harbors the hygromycin resistance gene under the control of *U. maydis* hsp 70 regulatory sequences.

NotI linkers were cloned into the SacI site in the polylinker of pHL1. pHLN is described in: Schulz, B., Banuett, F., Dahl, M., Schlesinger, R., Schäfer, W., Martin, T., Herskowitz, I., and Kahmann; R. (1990). The b alleles of *U. maydis*, whose combinations program pathogenic development, code for polypeptides containing a homeodomain-related motif. cell 60, 295–306.

These plasmids were transformed into the mutant, and the transformants were tested for complementation. It was possible in this case to identify a 25 kb XbaI fragment which complements the mutation. The 25 kb XbaI fragment is indicated in FIG. 1 and is located between positions XbaI (32600) and XbaI (14000).

A BglII fragment about 10 kb in size, which is likewise complementing and is depicted in the Figure between positions BglII (15,000) and BglII (5100), was found in the same way.

As depicted in FIG. 1, the two complementing fragments have an overlapping region.

It was possible in this way to limit the complementing region to an XbaI-BglII fragment 8.9 kb in size. This fragment contains the genetic information necessary for complementation. It is depicted in FIG. 1 between positions XbaI (14,000) and BglII (5100). On the fragment there are also a BamHI site at pos. 10600 and a ClaI site at position 6900.

EXAMPLE 5

Figure 2:
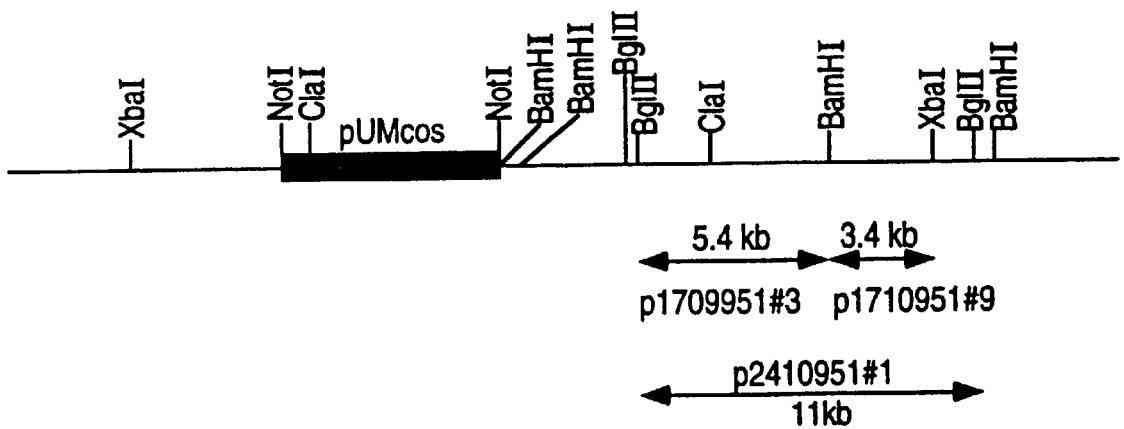
FIG. 2 depicts a section of the region of cosmid pUMcos7-H2 which harbors the XbaI-BglII nucleic acid fragment.

Determination of the Nucleic Acid Sequence of the Complementary XbaI-BglII Nucleic Acid Fragment A 5.4 kb BglII-BamHI fragment and a 3.4 kb BamHI-XbaI fragment were obtained from the XbaI-BglII fragment. Both fragments were cloned into the Blueskript vector (Stratagene). The nucleic acid sequence of the 5.4 kb BglII-BamHI insert of the clone p1709951#3 (FIG. 2) and of the 3.4 kb BamHI-XbaI insert of the clone p1710951#9 (FIG. 2) were determined by DNA sequencing (see FIG. 3). In addition, an 11 kb BglII fragment which comprises the region of the XbaI-BglII fragment was isolated from the cosmid pUMcos 7-H2 and was coloned into the pSL 1180 plasmid vector (Pharmacia). The clone was called p2410951#1 (FIG. 2). DNA sequencing of the clone p2410951#1 confirmed the sequence of the BglII-XbaI fragment (FIG. 3). A gene product having the amino acid sequence indicated in FIG. 4 was identified by analyzing the open reading frames. The corresponding DNA sequence is depicted in SEQ ID NO:1, and the amino acid sequence of the gene product is depicted in SEQ ID NO:2.

We claim:

1. A nucleic acid fragment from the fungus *Ustilago maydis*, which comprises the XbaI-BglII fragment depicted in FIG. 1.

2. A nucleic acid fragment as claimed in claim 1, which is capable of functional complementation of an *Ustilago maydis* mutant which constitutively expresses egl1.

3. A nucleic acid fragment which hybridizes under standard with a nucleic acid fragment as claimed in claim 1 and which is capable of functional complementation of an *Ustilago maydis* mutant which constitutively expresses egl1.

4. A method of identifying a potential fungicide, which method comprises bringing a haploid strain of *Ustilago maydis*, which strain comprises the XbaI-BglII nucleic acid fragment defined in claim 1, and which does not express endoglucanase egl1, into contact with a compound which is to be tested for fungicidal action; and measuring the amount of endoglucanase egl1 expressed by the haploid strain; wherein an increased expression of egl1 indicates that the tested compound is a fungicide.

5. The method of claim 4, wherein the site of action of the compound which is to be tested for fungicidal action is a gene product of the XbaI-BglII nucleic acid fragment.

6. The method of claim 4, wherein the site of action of the compound which is to be tested for fungicidal action is a gene product of the XbaI-BglII nucleic acid fragment which is represented by the amino acid sequence depicted in SEQ ID NO:2.

7. A method of producing a gall in a corn plant, wherein said gall lacks black discoloration, which method comprises infecting the corn plant with a strain of *Ustilago maydis* which harbors the nucleic acid fragment defined in claim 1; waiting for a gall lacking black discoloration to be formed; and recovering the formed gall.

8. A nucleic acid fragment as claimed in claim 1, having the nucleic acid sequence indicated in SEQ ID NO:1 between the BglII and the XbaI cleavage site.

9. The gene product of the nucleic acid fragment as claimed in claim 8, which is represented by the amino acid sequence depicted in SEQ ID NO:2.

10. A food product made from the galls of a corn plant, wherein said galls are caused by a strain of *Ustilago maydis* which harbors the nucleic acid fragment defined in claim 1.

* * * * *

UNITED STATES PATENT AND TRADEMARK OFFICE
CERTIFICATE OF CORRECTION

PATENT NO. : 6,103,229
DATED : August 15, 2000
INVENTOR(S) : Kahmann et al.

It is certified that error appears in the above-identified patent and that said Letters Patent is hereby corrected as shown below:

Column 33,
Line 25 bridging line 26, delete "under stan-dard".

Signed and Sealed this

Seventh Day of August, 2001

*Attest:*

*Attesting Officer*

NICHOLAS P. GODICI
*Acting Director of the United States Patent and Trademark Office*

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
        (A) LENGTH: 8931 base pairs
        (B) TYPE: Nucleic acid
        (C) STRANDEDNESS: double
        (D) TOPOLOGY: linear (xi) SEQUENCE DESCRIPTION: SEQ ID NO: 1:

```
AGATCTACAC TCTCTTTACG ACCGTCTGTC AGTTAATGTT TCAAAGCCGA GCATCGTCCT      60

GGATGCAGCT TGCTTTGCAG GCGTTAAAAC CACATTTTTT CGATTTCGCT CTTCTCTATC     120

AGTTGTTTCT TGATTATATC TCGTGATACG TTGCATACCT TGTACACGGG TCGCAATTTA     180

AGAGTTTCGT ATTCATGACA CTCGTGACTG ATCTTGGCTT GCTCAAAGTT GGTCGTGCTC     240

TGAAGACAGT GGCGATGCTA ACAGACGATG CGGTATACAG GGAGACAAGG GTATGTCACG     300

GTCGCTGGTT CGGAGATGTG TGAGCAGCAG GTGTGGACGC TAGCGATTCA GAGGTCGAAT     360

GAGCTCCTTC GCAACAAGGC GAGGCAAAGC GTCCGTCAAG GCAGGGCATG CTGATGAGGA     420

GCTGCCACGC GAGTCGCGCC GACAGCGAAG CACACATGAC GAGTCCCACG ACACGGTCGT     480

GGCCCGACGT CTACCACCGG TGCTGGTGTG TGCTGTAGGA TGATTTGGAC AGGGAGAGGA     540

AGGCACACGA CACGCGATCA GCTTGATAGC GAGCAACCCT TGTTCTGCTT GTTTTTGAAC     600

AGAGGGTGCT GTCATACGAG CGGCCAGACG CTGGCAATGG CCCACCGAAT GTGATGGAGG     660

AAAGCGCCAT GGCAAGGCGC AGGCTCAGGA ACGATAAGAT GGTTTGATTC CCTATTCGAC     720

ACACGAGTTG GCTATTAGTC GTGAGCGTGA GTCGTGAGTG TGACTGGCGA AACACGACAG     780

GTGCAGAGCT CGGCAACGAA CTTTCGACTT GCGCCCACTT TACGCGGAGG AGCCGGGCGA     840

GAGACAGCGA GGATGCTTGA AAAATAAAAC AGGACAGGAA TAACAACAAG TCGGCCATGC     900

TTGACAGTCG GTGCATTTGC AGTGTGTCTA ATTCTGCGAG GCATCACGCC TCCTGCCTTT     960

TTTCCTCCAA ACCCACCCTT CCTGGCAGAA AGTGAGGCAG CAGAGAGAGG AAAAGAGAGA    1020

AAGAGTCACG AGTGGGTGCC GCAATCACGA ATATATTAAT AATTCGAAAC CAAAACGCTT    1080

TACAAGCATC AAGCACGAAG CTTAGGCCCT GCGTAATTCA CGATTCACGA TTCACGATTC    1140

ACGATTGTGA CTTGGAGCCA AGGCTGTGGC CTCTGTCGCC TAACCCTTTT TTGACAGAGG    1200

CTTCTGAGCT TGAGCGTGGG TGCCACAAAC TTGTCACGGC CTCCGAAATC AGAGGTCCTC    1260
```

-continued

```
CTCATCATCT CAATTTTTTT TTGTGTTGGC GTGTCGTTCG CGCTAGCATC AAGACCATCA    1320

CCACCATATC GATCACCGCG GCTGTGCTGC TGTCCGCCGC CCTGTCAGTA CTGCTCCACG    1380

GTTCTCCTCA ATCTCCGCCT CGCTGTTGTG TTTGTCTTCC ACGGTGCTTC GCGCTCAGCT    1440

GCTGTGCTTT GATCACACAT CGGGGTCGAT TCCTAACTTG TGTAAGCGCC TTATCCCACC    1500

CAATTTGCCA AGTCGATACC GCCGTTCTAT CGCGGCTCTG GCCGGCGATT CTTGGCACTT    1560

TCCCAACAGT TGCCTTGTCG GACTAGCCGC AATCTTGGCT CACAACGTGC AAACTATCTG    1620

TCGAGATTCA TGACGGCGCT TCCCTAGTCA GGATCGGAAA ACGCCGCTCT CTCTGTGCCA    1680

CATCGATTTC GCCTGCCACC AAAGGTGCAC CTCTCTGTCT CTCCTGAATA CGTCCGCCGC    1740

TCATCTCAGC ATCCTTCTCC TCCGTTCTAT CTCCCTGCGC CTGCTGTTGT TCATCGATAT    1800

CCGCCAGCAT ACGAGACACA CGTTGGCAGC TCCTCGATCT CTAACC ATG ACA TCC       1855
                                                Met Thr Ser
                                                 1
```

```
ACC AAG ACA AGC TCT CAG CCC TCA GGC TCG AGT GAC ACT CCT CAA CGC    1903
Thr Lys Thr Ser Ser Gln Pro Ser Gly Ser Ser Asp Thr Pro Gln Arg
     5              10              15

ATC GTC GTC AAA TCC GTC AAT GGT CAC GAG CCC ATC AAA GTA GAG CCT    1951
Ile Val Val Lys Ser Val Asn Gly His Glu Pro Ile Lys Val Glu Pro
 20              25              30                  35

GTC TCC TCG TCC AGC GCA TCA CTG CTT CAC TCC ACA CCG CCC CGG CTC    1999
Val Ser Ser Ser Ser Ala Ser Leu Leu His Ser Thr Pro Pro Arg Leu
             40              45                  50

GCC ACA CCG CTT TCC TCA CCC ACC AAA TCA GCC GCC CCC TCG AGT CCA    2047
Ala Thr Pro Leu Ser Ser Pro Thr Lys Ser Ala Ala Pro Ser Ser Pro
         55              60                  65

TCC AAG TCT CCA GGA AGG GCG CGA CGT GTA GAT CCT GTC TTG ATC TCG    2095
Ser Lys Ser Pro Gly Arg Ala Arg Arg Val Asp Pro Val Leu Ile Ser
     70              75                  80

TCT CGC GAG TTT GGC CCT AGT GCT GGA GGA GAC AGC GAT GAC GAT GAG    2143
Ser Arg Glu Phe Gly Pro Ser Ala Gly Gly Asp Ser Asp Asp Asp Glu
         85              90              95

TTC AAC AAT GGC GAG CCC GAA GTT TAC AAG GGC GTC AAC ACC ACT GCC    2191
Phe Asn Asn Gly Glu Pro Glu Val Tyr Lys Gly Val Asn Thr Thr Ala
100             105             110             115

AAA AGG CTC AGC CGC AAG AGC AAG GCG GAT GCT ATG TTC GCC ATG TCC    2239
Lys Arg Leu Ser Arg Lys Ser Lys Ala Asp Ala Met Phe Ala Met Ser
        120             125             130

GTC AAA GAG TCT TCT CCC GTC CAT GCG CAC GCA ACA TCC ACA TCT ACC    2287
Val Lys Glu Ser Ser Pro Val His Ala His Ala Thr Ser Thr Ser Thr
    135             140             145

ACT TCA AAT GCT CCC ACT GCC ATC CCC GGC AAC CCT GCC TCC CAC CCA    2335
Thr Ser Asn Ala Pro Thr Ala Ile Pro Gly Asn Pro Ala Ser His Pro
        150             155             160

GCA CGC AAA ATG TTC CAG CAC CAG CCA TTT CCG CCT CTG GTT TTC GAT    2383
Ala Arg Lys Met Phe Gln His Gln Pro Phe Pro Pro Leu Val Phe Asp
    165             170             175

ACA GAT CCC ATC TCA TCC ATC TCG CAG TCT CCA TCC GCT TCC AAT GCG    2431
Thr Asp Pro Ile Ser Ser Ile Ser Gln Ser Pro Ser Ala Ser Asn Ala
180             185             190             195

GCT CAG CCC CCC ATT CCA ACT CAT GCC AGC ACG CCA CGC TGC CCT CCG    2479
Ala Gln Pro Pro Ile Pro Thr His Ala Ser Thr Pro Arg Cys Pro Pro
        200             205             210

CCC AGG CTC CGT CCC AGA CTC TTT GAG CTC GAC GAA GCG CCC ACT TTC    2527
Pro Arg Leu Arg Pro Arg Leu Phe Glu Leu Asp Glu Ala Pro Thr Phe
    215             220             225

TAT CCA TCG CCT GAA GAG TTC TCT GAT CCA ATG AAG TAC ATC GCC TGG    2575
```

-continued

```
              Tyr Pro Ser Pro Glu Glu Phe Ser Asp Pro Met Lys Tyr Ile Ala Trp
                          230                 235                 240

ATC GCC GAC CCA CAA GGT GGT AAT GGC AAG GCA TAC GGC ATC GTC AAG              2623
Ile Ala Asp Pro Gln Gly Gly Asn Gly Lys Ala Tyr Gly Ile Val Lys
        245                 250                 255

ATC GTT CCA CCT CAG GGC TGG AAC CCG GAA TGC GTG CTT GAT GAG CAG              2671
Ile Val Pro Pro Gln Gly Trp Asn Pro Glu Cys Val Leu Asp Glu Gln
260                 265                 270                 275

ACC TTC CGC TTT CGC ACC CGC GTT CAG CTC CTC AAC TCG CTC AGT GCA              2719
Thr Phe Arg Phe Arg Thr Arg Val Gln Leu Leu Asn Ser Leu Ser Ala
                280                 285                 290

GAT GCT CGG GCC TCT CAG AAC TAC CAG GAG CAA CTG CAA AAG TTC CAC              2767
Asp Ala Arg Ala Ser Gln Asn Tyr Gln Glu Gln Leu Gln Lys Phe His
            295                 300                 305

GCG CAG CAG GGT CGC AAG CGT GTC TCG GTC CCC GTC ATT GAC GGT CGT              2815
Ala Gln Gln Gly Arg Lys Arg Val Ser Val Pro Val Ile Asp Gly Arg
        310                 315                 320

TCC GTC GAT TTG TAC CAG CTC AAA CTA GTC ATC TCA AGT CTG GGT GGC              2863
Ser Val Asp Leu Tyr Gln Leu Lys Leu Val Ile Ser Ser Leu Gly Gly
    325                 330                 335

TAC GAT GCT GTT TGC CGT GCT CGC AAG TGG TCC GAT GCT ACG CGT AAG              2911
Tyr Asp Ala Val Cys Arg Ala Arg Lys Trp Ser Asp Ala Thr Arg Lys
340                 345                 350                 355

ATC GGC TAC AGT GAC AAG GAA AGC GGT CAG CTC TCG ACG CAA GTC AAA              2959
Ile Gly Tyr Ser Asp Lys Glu Ser Gly Gln Leu Ser Thr Gln Val Lys
                360                 365                 370

GCT GCC TAC ACC CGC ATC ATC TTG CCC TTT GAA GAG TTT CTT GCA AAA              3007
Ala Ala Tyr Thr Arg Ile Ile Leu Pro Phe Glu Glu Phe Leu Ala Lys
            375                 380                 385

GCA AAA GAG CAG TCT CGT CCT AAC GGA TCA TCG GTC AGC CCA CAG CTC              3055
Ala Lys Glu Gln Ser Arg Pro Asn Gly Ser Ser Val Ser Pro Gln Leu
        390                 395                 400

GCG CAG AGT GCC ATC ATG GGC GCC ACC GCC AGC ACG GAC ACC CAA GAG              3103
Ala Gln Ser Ala Ile Met Gly Ala Thr Ala Ser Thr Asp Thr Gln Glu
    405                 410                 415

AAT GGC GTT AAG CAC CCC TCC ATG TCG CCA AGC CTC GAC GCC GCC CCC              3151
Asn Gly Val Lys His Pro Ser Met Ser Pro Ser Leu Asp Ala Ala Pro
420                 425                 430                 435

AGT GGA GAT GCA GGT GAA CAC TTC AAA ACA CCC GAG CCT TTC ACT GCT              3199
Ser Gly Asp Ala Gly Glu His Phe Lys Thr Pro Glu Pro Phe Thr Ala
                440                 445                 450

GCT GGC GCT GCT GAG GCG CTC GCA AAT GCA ACT CCC GTC CTC GAG ACA              3247
Ala Gly Ala Ala Glu Ala Leu Ala Asn Ala Thr Pro Val Leu Glu Thr
            455                 460                 465

CCC ACT CAA AGC CCT TCG ACT GTC GCA AGC ACA CGT CGC AGT GCG CGC              3295
Pro Thr Gln Ser Pro Ser Thr Val Ala Ser Thr Arg Arg Ser Ala Arg
        470                 475                 480

AAG AGA TCG GAA GCA ACC AGC ACA CCT GCT TCG TCG TCG CGT AAC TCT              3343
Lys Arg Ser Glu Ala Thr Ser Thr Pro Ala Ser Ser Ser Arg Asn Ser
    485                 490                 495

TTG CAG CTC ACC TCC ACA CCA ATG ACA CCT TTG ATC TCC AGA CGC AGA              3391
Leu Gln Leu Thr Ser Thr Pro Met Thr Pro Leu Ile Ser Arg Arg Arg
500                 505                 510                 515

AAG GGC GTT AGC CCT CAC CTT GAA GCA GAT TCT TAC CTG CGC GCT CAA              3439
Lys Gly Val Ser Pro His Leu Glu Ala Asp Ser Tyr Leu Arg Ala Gln
                520                 525                 530

GCT GGC AAT CAG GCG CAA GAA GAG CAA ATG TGC GAA ATC TGC CTC CGA              3487
Ala Gly Asn Gln Ala Gln Glu Glu Gln Met Cys Glu Ile Cys Leu Arg
            535                 540                 545
```

```
GGC GAG GAT GGT CCC AAC ATG TTG CTC TGC GAC GAG TGC AAT CGT GGC      3535
Gly Glu Asp Gly Pro Asn Met Leu Leu Cys Asp Glu Cys Asn Arg Gly
        550                 555                 560

TAC CAC ATG TAC TGT CTC CAA CCC GCG CTC ACT TCG ATC CCC AAA TCG      3583
Tyr His Met Tyr Cys Leu Gln Pro Ala Leu Thr Ser Ile Pro Lys Ser
        565                 570                 575

CAG TGG TTC TGC CCG CCT TGT CTT GTC GGC ACC GGT CAT GAT TTT GGT      3631
Gln Trp Phe Cys Pro Pro Cys Leu Val Gly Thr Gly His Asp Phe Gly
580                 585                 590                 595

TTT GAC GAT GGT GAA ACA CAC AGC CTC TAC ACT TTT TGG CAA CGT GCT      3679
Phe Asp Asp Gly Glu Thr His Ser Leu Tyr Thr Phe Trp Gln Arg Ala
                600                 605                 610

GAG GCA TTC AAG CGC GAT TGG TGG TCC AAA CAT CAA GAT CAC CTC TGG      3727
Glu Ala Phe Lys Arg Asp Trp Trp Ser Lys His Gln Asp His Leu Trp
        615                 620                 625

AGG CCC GAC TCG GAA GGC CTG GCG ACA TCT GAC TAC GAT CCG CCA ACG      3775
Arg Pro Asp Ser Glu Gly Leu Ala Thr Ser Asp Tyr Asp Pro Pro Thr
        630                 635                 640

AAT GGT CTG GCT CGC CGT GTC CAC GGA ACC GAC CTG GTT GTG TCA GAG      3823
Asn Gly Leu Ala Arg Arg Val His Gly Thr Asp Leu Val Val Ser Glu
645                 650                 655

GAC GAC GTA GAG CGC GAA TTT TGG AGA CTA GTT CAT AGC CAG AAG GAA      3871
Asp Asp Val Glu Arg Glu Phe Trp Arg Leu Val His Ser Gln Lys Glu
660                 665                 670                 675

GAA GTA GAA GTC GAG TAT GGT GCT GAC GTT CAC TCT ACT ACG CAC GGC      3919
Glu Val Glu Val Glu Tyr Gly Ala Asp Val His Ser Thr Thr His Gly
                680                 685                 690

AGT GCC TTG CCC ACC CAA GAG ACT CAT CCC TTG AGT CTG TAT TCG CGC      3967
Ser Ala Leu Pro Thr Gln Glu Thr His Pro Leu Ser Leu Tyr Ser Arg
        695                 700                 705

GAC AAG TGG AAC CTC AAT AAC CTA CCC ATC CTG CCT GGC TCG CTG CTC      4015
Asp Lys Trp Asn Leu Asn Asn Leu Pro Ile Leu Pro Gly Ser Leu Leu
        710                 715                 720

CAG TAC ATC AAG TCC GAC ATC TCG GGC ATG ACC GTC CCC TGG ATC TAT      4063
Gln Tyr Ile Lys Ser Asp Ile Ser Gly Met Thr Val Pro Trp Ile Tyr
        725                 730                 735

GTC GGA ATG ATT TTC TCC ACC TTC TGC TGG CAC AAC GAG GAT CAC TAC      4111
Val Gly Met Ile Phe Ser Thr Phe Cys Trp His Asn Glu Asp His Tyr
740                 745                 750                 755

ACT TAC TCG ATC AAC TAT CAG CAT TGG GGT GAG ACT AAG ACA TGG TAC      4159
Thr Tyr Ser Ile Asn Tyr Gln His Trp Gly Glu Thr Lys Thr Trp Tyr
                760                 765                 770

GGC ATT CCG GGT GAA GAT GCC GAA AAG TTC GAG AAT GCC ATG CGC AAG      4207
Gly Ile Pro Gly Glu Asp Ala Glu Lys Phe Glu Asn Ala Met Arg Lys
        775                 780                 785

GCG GCG CCC GAT TTA TTC GAG ACG CTG CCG GAC CTG CTC TTT CAT CTC      4255
Ala Ala Pro Asp Leu Phe Glu Thr Leu Pro Asp Leu Leu Phe His Leu
        790                 795                 800

ACC ACC ATG ATG AGT CCC GAG AAG CTC AAG AAG GAA GGC GTC CGC GTT      4303
Thr Thr Met Met Ser Pro Glu Lys Leu Lys Lys Glu Gly Val Arg Val
805                 810                 815

GTG GCA TGT GAC CAA CGT GCC AAC GAG TTT GTC GTC ACT TTT CCC AAG      4351
Val Ala Cys Asp Gln Arg Ala Asn Glu Phe Val Val Thr Phe Pro Lys
820                 825                 830                 835

GCC TAC CAC AGC GGC TTT AAC CAC GGT CTC AAC CTG AAT GAA GCT GTC      4399
Ala Tyr His Ser Gly Phe Asn His Gly Leu Asn Leu Asn Glu Ala Val
                840                 845                 850

AAC TTT GCT CTG CCC GAC TGG ATC TTT GAC GAT CTC GAA TCT GTT CGG      4447
Asn Phe Ala Leu Pro Asp Trp Ile Phe Asp Asp Leu Glu Ser Val Arg
        855                 860                 865
```

-continued

```
AGG TAC CAG CGC TTC CGA AAG CCT GCC GTA TTC TCA CAC GAC CAG CTG         4495
Arg Tyr Gln Arg Phe Arg Lys Pro Ala Val Phe Ser His Asp Gln Leu
        870                 875                 880

CTC ATT ACC GTC TCG CAG CAG AGT CAG ACC ATC GAA ACA GCC GTG TGG         4543
Leu Ile Thr Val Ser Gln Gln Ser Gln Thr Ile Glu Thr Ala Val Trp
    885                 890                 895

CTT GAG GCC GCC ATG CAA GAG ATG GTT GAT CGC GAG ATC GCA AAG CGC         4591
Leu Glu Ala Ala Met Gln Glu Met Val Asp Arg Glu Ile Ala Lys Arg
900                 905                 910                 915

AAC GCA CTT CGT GAG ATC ATT CCG GAT CTC AAA GAA GAG GTA TAC GAC         4639
Asn Ala Leu Arg Glu Ile Ile Pro Asp Leu Lys Glu Glu Val Tyr Asp
                920                 925                 930

GAA GAT GTA GCC GAG AGC CAC TAC ATT TGC AGC CAC TGC ACT CTC TTT         4687
Glu Asp Val Ala Glu Ser His Tyr Ile Cys Ser His Cys Thr Leu Phe
            935                 940                 945

TCC TAC CTC GGC CAG TTG ACA AGT CCA AAG ACC GAT GGT GTC GCT TGT         4735
Ser Tyr Leu Gly Gln Leu Thr Ser Pro Lys Thr Asp Gly Val Ala Cys
        950                 955                 960

CTC GAT CAC GGC TTC GAG GTG TGC AAC GCC GAT GCT CCC GTC AAG TGG         4783
Leu Asp His Gly Phe Glu Val Cys Asn Ala Asp Ala Pro Val Lys Trp
    965                 970                 975

ACG TTG AAG CTT CGC TTC TCG GAC GAT CAG CTT CGC TCC ATT CTA GCG         4831
Thr Leu Lys Leu Arg Phe Ser Asp Asp Gln Leu Arg Ser Ile Leu Ala
980                 985                 990                 995

AAG GTC TGT GAG CGG GCA GCA GTG CCG CGC AAC TGG ATT CAG CGC CTC         4879
Lys Val Cys Glu Arg Ala Ala Val Pro Arg Asn Trp Ile Gln Arg Leu
                1000                1005                1010

AAG AAG ACC CTT GCT CTT GGC CCG ACT CCA CCT CTC AAG ACG CTG AGG         4927
Lys Lys Thr Leu Ala Leu Gly Pro Thr Pro Pro Leu Lys Thr Leu Arg
            1015                1020                1025

TCG TTG CTG CAC GAA GGC GAA AAG ATT GCC TTC TCG CTA GAG CCG CTC         4975
Ser Leu Leu His Glu Gly Glu Lys Ile Ala Phe Ser Leu Glu Pro Leu
        1030                1035                1040

GAG GAT CTC AGG ACC TTT GTC ACC TGC GCC AAC TCG TGG GTG GAG CGG         5023
Glu Asp Leu Arg Thr Phe Val Thr Cys Ala Asn Ser Trp Val Glu Arg
    1045                1050                1055

GCC AAT GTT TTC CTG ATG CGC AAG TTG CAT AAG AGA CGC GGC GAG CCT         5071
Ala Asn Val Phe Leu Met Arg Lys Leu His Lys Arg Arg Gly Glu Pro
1060                1065                1070                1075

GCA GCT GCT CCT GCT GGG AGG CGC CGA CGA TCC AAG GGC GGT GCT GTG         5119
Ala Ala Ala Pro Ala Gly Arg Arg Arg Arg Ser Lys Gly Gly Ala Val
                1080                1085                1090

GCT GAC GAT AGC TTC ACT AGA AGG CAA AGC TTG GAC GCT TCG GTC GAC         5167
Ala Asp Asp Ser Phe Thr Arg Arg Gln Ser Leu Asp Ala Ser Val Asp
            1095                1100                1105

GAT GCC GAA TCC ACT TCC GAT CGA AGT CCC GAA GCC TTG TAT GCG TTG         5215
Asp Ala Glu Ser Thr Ser Asp Arg Ser Pro Glu Ala Leu Tyr Ala Leu
        1110                1115                1120

ATC GGA GAG CTC GAC AGC CTT CAC TTT GAC GCG CCT GAG ATT GCA TCG         5263
Ile Gly Glu Leu Asp Ser Leu His Phe Asp Ala Pro Glu Ile Ala Ser
    1125                1130                1135

CTT CGC ACT ATG GCG CAA GAG CTC GAG GAG TTC ATT GGC CGG TGT GAC         5311
Leu Arg Thr Met Ala Gln Glu Leu Glu Glu Phe Ile Gly Arg Cys Asp
1140                1145                1150                1155

GAG GTC CTA CAA CAG GGT GAC GAG ACT AAT CTC AAA GAC TGT GAA AGC         5359
Glu Val Leu Gln Gln Gly Asp Glu Thr Asn Leu Lys Asp Cys Glu Ser
                1160                1165                1170

ATC CTG ACG CTC GGC AGC TCT CTC AAT GTG GAC GCG CCT CAG ATC AAA         5407
Ile Leu Thr Leu Gly Ser Ser Leu Asn Val Asp Ala Pro Gln Ile Lys
```

-continued

```
           1175                1180                1185
GAG CTC TCC GAC TAT GTC GAG CGT CGC AAG TGG ATC CAG GAA GTC ACA    5455
Glu Leu Ser Asp Tyr Val Glu Arg Arg Lys Trp Ile Gln Glu Val Thr
        1190                1195                1200

GAA TCG TTC GAC ACA TAT CTC TAT TAC CAC GAA GTT GCG GAA CTG TTG    5503
Glu Ser Phe Asp Thr Tyr Leu Tyr Tyr His Glu Val Ala Glu Leu Leu
        1205                1210                1215

GAT CGC GCC GAC AGC TGT GGT CTA CAA GAT CAC GAG CTG CGC AAG AAT    5551
Asp Arg Ala Asp Ser Cys Gly Leu Gln Asp His Glu Leu Arg Lys Asn
1220                1225                1230                1235

CTT GAG CAG AGA CTC GAA GCC GGC CAA CGC TGG ACT GAA AGT GCA AGG    5599
Leu Glu Gln Arg Leu Glu Ala Gly Gln Arg Trp Thr Glu Ser Ala Arg
                1240                1245                1250

GAA GCG CTG GGA GGC TCT CAG CCT ATA ACA ATC GAC GTG CTT CAA GAG    5647
Glu Ala Leu Gly Gly Ser Gln Pro Ile Thr Ile Asp Val Leu Gln Glu
            1255                1260                1265

CTT TCC GAG TCG TCA GCT GAT GTT CCT GTT GTG CTC GAA GTG GCT CAG    5695
Leu Ser Glu Ser Ser Ala Asp Val Pro Val Val Leu Glu Val Ala Gln
        1270                1275                1280

GAT GTT ACC GAC GCT CTC TCC AAG GCC AAA GAG CTG CAA AAG ACC ATC    5743
Asp Val Thr Asp Ala Leu Ser Lys Ala Lys Glu Leu Gln Lys Thr Ile
1285                1290                1295

CAG ACA CTG TAC AAG GCA TTA CAG ACG GGA GCT CAC GGC CAT TCT GCA    5791
Gln Thr Leu Tyr Lys Ala Leu Gln Thr Gly Ala His Gly His Ser Ala
1300            1305                1310                1315

GCC GAT GCG GAT GGT GAC CTA TCA ATG ATC TCG ATC TCG GAA AAT GGC    5839
Ala Asp Ala Asp Gly Asp Leu Ser Met Ile Ser Ile Ser Glu Asn Gly
                1320                1325                1330

GAA GCT GCC GAG CGT GTG GCT CTG CTT CCT GAC GCT CGT CGC GTG CTT    5887
Glu Ala Ala Glu Arg Val Ala Leu Leu Pro Asp Ala Arg Arg Val Leu
            1335                1340                1345

CGT GCC GCC AGG TCC AAC AAA CTG GAG CTT GAG CAC GCG CAA GAC ATT    5935
Arg Ala Ala Arg Ser Asn Lys Leu Glu Leu Glu His Ala Gln Asp Ile
        1350                1355                1360

GAA AAG GCC GTC CAA GTC TAC GAT GCA TGG CGA GCT GCG TTC AAC CAG    5983
Glu Lys Ala Val Gln Val Tyr Asp Ala Trp Arg Ala Ala Phe Asn Gln
    1365                1370                1375

ATC ATG CAG ACT ATT GCC GGT GGA TCT CGC CGC CTC ACG GAC GCA GAC    6031
Ile Met Gln Thr Ile Ala Gly Gly Ser Arg Arg Leu Thr Asp Ala Asp
 1380               1385                1390                1395

CGC GAC GAG GAG CTC GAC AAG CTG GTG GAG CGA GTC GAG GAT GCC ACC    6079
Arg Asp Glu Glu Leu Asp Lys Leu Val Glu Arg Val Glu Asp Ala Thr
                1400                1405                1410

GAC CCT GCC GAC GAC CAG AAC AAA CCC AAT GCA CGC AAC TGT ATC TGC    6127
Asp Pro Ala Asp Asp Gln Asn Lys Pro Asn Ala Arg Asn Cys Ile Cys
            1415                1420                1425

AGG AGC TCA ATG CCC ATC GCC ATT CCT TCG TCG TCA GGG GCA GAA TGC    6175
Arg Ser Ser Met Pro Ile Ala Ile Pro Ser Ser Ser Gly Ala Glu Cys
        1430                1435                1440

TCT CGC TGT CGC GTG CAG TAC CAT CTA TCG TGC ATC AAG GTG CGC TCC    6223
Ser Arg Cys Arg Val Gln Tyr His Leu Ser Cys Ile Lys Val Arg Ser
    1445                1450                1455

TCT GAG GTA TCA CGC GCC GAG GGC GGC TGG GTT TGT CCA TTC TGC CCG    6271
Ser Glu Val Ser Arg Ala Glu Gly Gly Trp Val Cys Pro Phe Cys Pro
1460                1465                1470                1475

TGG TAC GGG AGC GCT CCG TTC CTC AAA ATG CGC AAG GCG ATC AGC ATT    6319
Trp Tyr Gly Ser Ala Pro Phe Leu Lys Met Arg Lys Ala Ile Ser Ile
                1480                1485                1490

GCT GAC CTT TCG AAG CTT GTA TAC GAT CAA GAT CAT CGT CGA GAC CAG    6367
```

```
                                                        -continued

Ala Asp Leu Ser Lys Leu Val Tyr Asp Gln Asp His Arg Arg Asp Gln
            1495                1500                1505

TTC AAA TTC CTC CCT CTG GAA TGG GAC GCC ATC GAG GAA GTG GTT GCC     6415
Phe Lys Phe Leu Pro Leu Glu Trp Asp Ala Ile Glu Glu Val Val Ala
        1510                1515                1520

AAG GCA AAG CGA TTC GAG ACG GCC GCT AAG CGA ATG ATC AAA ACA CTT     6463
Lys Ala Lys Arg Phe Glu Thr Ala Ala Lys Arg Met Ile Lys Thr Leu
    1525                1530                1535

TCG CTG ATG CGC AGA GAT CAA AAG CAG GTC ATC CTT GCC CAC TGG CTA     6511
Ser Leu Met Arg Arg Asp Gln Lys Gln Val Ile Leu Ala His Trp Leu
1540                1545                1550                1555

CGT CGG TCC ATT GGC TGC CCC GTC GAT GTC TTG GGA CCA GAG AAA GTC     6559
Arg Arg Ser Ile Gly Cys Pro Val Asp Val Leu Gly Pro Glu Lys Val
                1560                1565                1570

AAC ATG CTT GAC CTC ATC AGC GAA AAT TTG CTC GCC CTT GGT TCA CAG     6607
Asn Met Leu Asp Leu Ile Ser Glu Asn Leu Leu Ala Leu Gly Ser Gln
            1575                1580                1585

CAG GGT GAT GCT GCA CCC ATG GCG CCT GTT GAG CGT ATC AAG GCG TCG     6655
Gln Gly Asp Ala Ala Pro Met Ala Pro Val Glu Arg Ile Lys Ala Ser
        1590                1595                1600

ACT CCA GCG CGA TCC GAC GAG CGC ACG GAA GAA ACA ACG CCC TTG CCT     6703
Thr Pro Ala Arg Ser Asp Glu Arg Thr Glu Glu Thr Thr Pro Leu Pro
    1605                1610                1615

CGC TCG TCT CGC GTT CCA GCC CCT GCC GAT CGC GAC TCA GGA TCT CCA     6751
Arg Ser Ser Arg Val Pro Ala Pro Ala Asp Arg Asp Ser Gly Ser Pro
1620                1625                1630                1635

GCT GTC CGA GAC GAT CGC AAG CGC AAA GCC AAG AGA GGC AAG CGT GCC     6799
Ala Val Arg Asp Asp Arg Lys Arg Lys Ala Lys Arg Gly Lys Arg Ala
                1640                1645                1650

AAG CTC GTC TTC CAG GAG GAG ATT GGT ATC GGT GCT TAC CGC GAT CGT     6847
Lys Leu Val Phe Gln Glu Glu Ile Gly Ile Gly Ala Tyr Arg Asp Arg
            1655                1660                1665

CAG CCC ATC TAC TGT CTG TGC CAT GAG CCA GAG AGC GGT CGC ATG ATT     6895
Gln Pro Ile Tyr Cys Leu Cys His Glu Pro Glu Ser Gly Arg Met Ile
        1670                1675                1680

GCT TGT GAC AAG TGC ATG CTC TGG TTT CAT ACC AAT TGT GTT CGC CTC     6943
Ala Cys Asp Lys Cys Met Leu Trp Phe His Thr Asn Cys Val Arg Leu
    1685                1690                1695

GAT GAT CCG CCG AAT CTC GGA AAT GAG CCG TGG ATA TGT CCC ATG TGC     6991
Asp Asp Pro Pro Asn Leu Gly Asn Glu Pro Trp Ile Cys Pro Met Cys
1700                1705                1710                1715

TGC ATC AAG GCG GAG CGC AAG TAT CCT CAG GCC GAA GTC AGG GTC AAA     7039
Cys Ile Lys Ala Glu Arg Lys Tyr Pro Gln Ala Glu Val Arg Val Lys
                1720                1725                1730

GAC ATT GGC GTC ACC GAC CCG GAT CTG TGG CTC GAC ATC CGT GCC ACG     7087
Asp Ile Gly Val Thr Asp Pro Asp Leu Trp Leu Asp Ile Arg Ala Thr
            1735                1740                1745

CTG CGA TCG CTC GAG AAG CCT GTC AGC AAG ATT CAG TCG TGG ACC AGC     7135
Leu Arg Ser Leu Glu Lys Pro Val Ser Lys Ile Gln Ser Trp Thr Ser
        1750                1755                1760

CCG GAG AAC AAG CGC ATT GTG CTA CAT CTG GAA AAG TTC ACA CCG GCT     7183
Pro Glu Asn Lys Arg Ile Val Leu His Leu Glu Lys Phe Thr Pro Ala
    1765                1770                1775

ATC CAT GCT GAG GAG GTG CAC TCG CAG ATC ACC AAA CGT GCG CGT CTC     7231
Ile His Ala Glu Glu Val His Ser Gln Ile Thr Lys Arg Ala Arg Leu
1780                1785                1790                1795

GAG TCC GAC ACG CCG AGC AAG GCG CGA GTG TCT CTG GGC CGC TCT GAT     7279
Glu Ser Asp Thr Pro Ser Lys Ala Arg Val Ser Leu Gly Arg Ser Asp
                1800                1805                1810
```

-continued

| | |
|---|---|
| TCG ATC TCG ACG CCA GCA AAG GAG AGC GGC GCC GTT CCT TAT GCG GCA<br>Ser Ile Ser Thr Pro Ala Lys Glu Ser Gly Ala Val Pro Tyr Ala Ala<br>               1815                           1820                         1825 | 7327 |
| GCT CCT GTG CCC AGC GAG GCT GTT CGA GGT ATC GTG CCT GCT TTG ACG<br>Ala Pro Val Pro Ser Glu Ala Val Arg Gly Ile Val Pro Ala Leu Thr<br>               1830                           1835                         1840 | 7375 |
| CCG GCG GCT GAT TCA CCC GCC TCC AGA TCA GGA AGG AAC GAC GAT TCA<br>Pro Ala Ala Asp Ser Pro Ala Ser Arg Ser Gly Arg Asn Asp Asp Ser<br>               1845                           1850                         1855 | 7423 |
| TTT GCT GCA GCC TCG CCT CCT TTG TGG GAT GCC AAG ACT GGA CCA TCT<br>Phe Ala Ala Ala Ser Pro Pro Leu Trp Asp Ala Lys Thr Gly Pro Ser<br>1860                         1865                           1870                         1875 | 7471 |
| CCT GGC AAC GCC AGC ATC GAA TGG GCG CAG TCG GCA CGT CGA CGA TAT<br>Pro Gly Asn Ala Ser Ile Glu Trp Ala Gln Ser Ala Arg Arg Arg Tyr<br>                          1880                           1885                         1890 | 7519 |
| GCC GAA GGC ATG GAC AAC CTC TAC CGT CGC GGC ATC ACG GAC ACG ATG<br>Ala Glu Gly Met Asp Asn Leu Tyr Arg Arg Gly Ile Thr Asp Thr Met<br>               1895                           1900                         1905 | 7567 |
| CTG GTG CGA TTC TAC GTT GGA TGG AAT GGA CGT ACG CTC TTT CAT CCG<br>Leu Val Arg Phe Tyr Val Gly Trp Asn Gly Arg Thr Leu Phe His Pro<br>               1910                           1915                         1920 | 7615 |
| GTA CGA GAC TCA GCG GGC AAC ATT GTA GAG GTA TCT CTG GGC GAG AAC<br>Val Arg Asp Ser Ala Gly Asn Ile Val Glu Val Ser Leu Gly Glu Asn<br>               1925                           1930                         1935 | 7663 |
| GTC CGT CTG CAT CCA GAT GAT CCC GAG GGC GTG CGG GTA ATT CGT GCT<br>Val Arg Leu His Pro Asp Asp Pro Glu Gly Val Arg Val Ile Arg Ala<br>1940                         1945                           1950                         1955 | 7711 |
| GCC ATT GAA CGA CAC AGC GTC AAA GCG GAC CGT TTA GCC GCA AGT CAT<br>Ala Ile Glu Arg His Ser Val Lys Ala Asp Arg Leu Ala Ala Ser His<br>                          1960                           1965                         1970 | 7759 |
| GGC TAT GGC GGC GAG ATG GAC GAT CAT GTG TAC TCT CGC AAC GCT TAC<br>Gly Tyr Gly Gly Glu Met Asp Asp His Val Tyr Ser Arg Asn Ala Tyr<br>               1975                           1980                         1985 | 7807 |
| AGT CGC GAC GAC GGA CGC TAT ACA GCT CAG CGA CGC GAT CCT CCG GTG<br>Ser Arg Asp Asp Gly Arg Tyr Thr Ala Gln Arg Arg Asp Pro Pro Val<br>               1990                           1995                         2000 | 7855 |
| GTA CCG TCG AAT GGC AGA TTC AGC ATG AGA TCG CCT GCC ACG ATT CCT<br>Val Pro Ser Asn Gly Arg Phe Ser Met Arg Ser Pro Ala Thr Ile Pro<br>               2005                           2010                         2015 | 7903 |
| TCG CAA CGA CTT GGC AGC GAT CGC GAC TAT GAA CGC GAG CGG GAG CGT<br>Ser Gln Arg Leu Gly Ser Asp Arg Asp Tyr Glu Arg Glu Arg Glu Arg<br>2020                         2025                           2030                         2035 | 7951 |
| GAC GGG GAT CTT CAT GAT GCC CGT GAT GGT CGT GAT GGC CGA TAT GGC<br>Asp Gly Asp Leu His Asp Ala Arg Asp Gly Arg Asp Gly Arg Tyr Gly<br>                          2040                           2045                         2050 | 7999 |
| GAT TCA TTA CGT TCT CCG GCG GCA CCA GTG GCG GCG ATG ACT GCC CCT<br>Asp Ser Leu Arg Ser Pro Ala Ala Pro Val Ala Ala Met Thr Ala Pro<br>               2055                           2060                         2065 | 8047 |
| GGT gca ttg gac acc tcg ccg gcg ctc cga acg aat cta gcg cgc gaa<br>Gly Ala Leu Asp Thr Ser Pro Ala Leu Arg Thr Asn Leu Ala Arg Glu<br>             2070                           2075                         2080 | 8095 |
| GTC GTG CCG ACA TAC GCG CGA AGC TCA GCT AAT GCA TCG GCA ACC ACA<br>Val Val Pro Thr Tyr Ala Arg Ser Ser Ala Asn Ala Ser Ala Thr Thr<br>               2085                           2090                         2095 | 8143 |
| AGT CCA TAC ACT GGC GCT GCT TCG ACG TAC AGC ATT TAT TCG GCA TCT<br>Ser Pro Tyr Thr Gly Ala Ala Ser Thr Tyr Ser Ile Tyr Ser Ala Ser<br>2100                         2105                           2110                         2115 | 8191 |
| GAC AGA GCG GCA TCT TAT CCG GTG GGT CGC AGT TCG ATT TCG CAG GCG<br>Asp Arg Ala Ala Ser Tyr Pro Val Gly Arg Ser Ser Ile Ser Gln Ala<br>                          2120                           2125                         2130 | 8239 |

```
GAT CTG GAT GGA AAT AGG GGG GGA CCT CCA CCG ATG GCG ATG TAT GCT      8287
Asp Leu Asp Gly Asn Arg Gly Gly Pro Pro Pro Met Ala Met Tyr Ala
             2135                2140                2145

TCT GCC AAG GCT GAG CCT GTC GCA AAT GGG TCT ACG TTT TCG GCA CTG      8335
Ser Ala Lys Ala Glu Pro Val Ala Asn Gly Ser Thr Phe Ser Ala Leu
             2150                2155                2160

GAC CCA GCG ATG ATG GCA GAC GAT GCA GCA GGA CAG ATC GAT CCC AAT      8383
Asp Pro Ala Met Met Ala Asp Asp Ala Ala Gly Gln Ile Asp Pro Asn
             2165                2170                2175

TTG ACG AGC AGT CCG GTT CTA GCT TCC AAC TCG GCA GTT CCC GCA CCG      8431
Leu Thr Ser Ser Pro Val Leu Ala Ser Asn Ser Ala Val Pro Ala Pro
2180                2185                2190                2195

TCG ACC GCA CCG GCA GCA GCA CAT GGT GTT CGG AGC GAG ACG AGG AGC      8479
Ser Thr Ala Pro Ala Ala Ala His Gly Val Arg Ser Glu Thr Arg Ser
                2200                2205                2210

CGT CCA CCC AGC GCA GGC AAC GAA GTC GCC CAT GAA GCC GGT TCC GCG      8527
Arg Pro Pro Ser Ala Gly Asn Glu Val Ala His Glu Ala Gly Ser Ala
             2215                2220                2225

AAA GCA CCC CCG GGT GCA CCC TCG GGT GGC CAC AGT GGC GAG ATC AAG      8575
Lys Ala Pro Pro Gly Ala Pro Ser Gly Gly His Ser Gly Glu Ile Lys
             2230                2235                2240

GAG CAC AAC CCA GAC GAG CAC GAG CTC GAG AGT GTT CGT CAG CAG GCT      8623
Glu His Asn Pro Asp Glu His Glu Leu Glu Ser Val Arg Gln Gln Ala
             2245                2250                2255

AGA CAG ATG GCG CGG AAA ATG CGA CCA GAC GCT TCC GAG GCC GAC ATC      8671
Arg Gln Met Ala Arg Lys Met Arg Pro Asp Ala Ser Glu Ala Asp Ile
2260                2265                2270                2275

GAA CGA TTG GTT CAA AAC TTT ATC GGT GGT GGA GAG TCT AAG TAG          8716
Glu Arg Leu Val Gln Asn Phe Ile Gly Gly Gly Glu Ser Lys
             2280                2285                2290

CGCGCCCTGC CAAGAATACA TGCGGTTCAA TGAAATTGTG AATCAAGAAT CATGAATCGT    8776

GAATGTACAA TCGATATCAC ACCACGCAGC ACGAATAGCG AGATTCACGA TTCACGAATC    8836

GTGATTCGTG AATCACGAAT GTGCGAACGA AAATCAGGGT TTGGATTCCA AGAGAAAGAA    8896

GCTGATGAAA CAGTGATGAG TCAAACGAGT CTAGA                               8931

(2) INFORMATION FOR SEQ ID NO: 2:

(i) SEQUENCE CHARACTERISTICS:
        (A) LENGTH: 2289 amino acids
        (B) TYPE: amino acid
        (D) TOPOLOGY: linear (xi) SEQUENCE DESCRIPTION: SEQ ID NO: 2:

Met Thr Ser Thr Lys Thr Ser Ser Gln Pro Ser Gly Ser Ser Asp Thr
1               5                   10                  15

Pro Gln Arg Ile Val Val Lys Ser Val Asn Gly His Glu Pro Ile Lys
            20                  25                  30

Val Glu Pro Val Ser Ser Ser Ala Ser Leu Leu His Ser Thr Pro
        35                  40                  45

Pro Arg Leu Ala Thr Pro Leu Ser Ser Pro Thr Lys Ser Ala Ala Pro
    50                  55                  60

Ser Ser Pro Ser Lys Ser Pro Gly Arg Ala Arg Arg Val Asp Pro Val
65                  70                  75                  80

Leu Ile Ser Ser Arg Glu Phe Gly Pro Ser Ala Gly Gly Asp Ser Asp
                85                  90                  95

Asp Asp Glu Phe Asn Asn Gly Glu Pro Glu Val Tyr Lys Gly Val Asn
            100                 105                 110
```

-continued

```
Thr Thr Ala Lys Arg Leu Ser Arg Lys Ser Lys Ala Asp Ala Met Phe
        115                 120                 125

Ala Met Ser Val Lys Glu Ser Ser Pro Val His Ala His Ala Thr Ser
    130                 135                 140

Thr Ser Thr Thr Ser Asn Ala Pro Thr Ala Ile Pro Gly Asn Pro Ala
145                 150                 155                 160

Ser His Pro Ala Arg Lys Met Phe Gln His Gln Pro Phe Pro Pro Leu
                165                 170                 175

Val Phe Asp Thr Asp Pro Ile Ser Ser Ile Ser Gln Ser Pro Ser Ala
            180                 185                 190

Ser Asn Ala Ala Gln Pro Pro Ile Pro Thr His Ala Ser Thr Pro Arg
    195                 200                 205

Cys Pro Pro Pro Arg Leu Arg Pro Arg Leu Phe Glu Leu Asp Glu Ala
210                 215                 220                 225

Pro Thr Phe Tyr Pro Ser Pro Glu Glu Phe Ser Asp Pro Met Lys Tyr
                230                 235                 240

Ile Ala Trp Ile Ala Asp Pro Gln Gly Gly Asn Gly Lys Ala Tyr Gly
            245                 250                 255

Ile Val Lys Ile Val Pro Pro Gln Gly Trp Asn Pro Glu Cys Val Leu
        260                 265                 270

Asp Glu Gln Thr Phe Arg Phe Arg Thr Arg Val Gln Leu Leu Asn Ser
    275                 280                 285

Leu Ser Ala Asp Ala Arg Ala Ser Gln Asn Tyr Gln Glu Gln Leu Gln
290                 295                 300                 305

Lys Phe His Ala Gln Gln Gly Arg Lys Arg Val Ser Val Pro Val Ile
                310                 315                 320

Asp Gly Arg Ser Val Asp Leu Tyr Gln Leu Lys Leu Val Ile Ser Ser
            325                 330                 335

Leu Gly Gly Tyr Asp Ala Val Cys Arg Ala Arg Lys Trp Ser Asp Ala
        340                 345                 350

Thr Arg Lys Ile Gly Tyr Ser Asp Lys Glu Ser Gly Gln Leu Ser Thr
    355                 360                 365

Gln Val Lys Ala Ala Tyr Thr Arg Ile Ile Leu Pro Phe Glu Glu Phe
370                 375                 380                 385

Leu Ala Lys Ala Lys Glu Gln Ser Arg Pro Asn Gly Ser Ser Val Ser
                390                 395                 400

Pro Gln Leu Ala Gln Ser Ala Ile Met Gly Ala Thr Ala Ser Thr Asp
            405                 410                 415

Thr Gln Glu Asn Gly Val Lys His Pro Ser Met Ser Pro Ser Leu Asp
        420                 425                 430

Ala Ala Pro Ser Gly Asp Ala Gly Glu His Phe Lys Thr Pro Glu Pro
    435                 440                 445

Phe Thr Ala Ala Gly Ala Ala Glu Ala Leu Ala Asn Ala Thr Pro Val
450                 455                 460                 465

Leu Glu Thr Pro Thr Gln Ser Pro Ser Thr Val Ala Ser Thr Arg Arg
                470                 475                 480

Ser Ala Arg Lys Arg Ser Glu Ala Thr Ser Thr Pro Ala Ser Ser Ser
            485                 490                 495

Arg Asn Ser Leu Gln Leu Thr Ser Thr Pro Met Thr Pro Leu Ile Ser
        500                 505                 510

Arg Arg Arg Lys Gly Val Ser Pro His Leu Glu Ala Asp Ser Tyr Leu
    515                 520                 525
```

-continued

```
Arg Ala Gln Ala Gly Asn Gln Ala Gln Glu Glu Gln Met Cys Glu Ile
530                 535                 540                 545

Cys Leu Arg Gly Glu Asp Gly Pro Asn Met Leu Leu Cys Asp Glu Cys
            550                 555                 560

Asn Arg Gly Tyr His Met Tyr Cys Leu Gln Pro Ala Leu Thr Ser Ile
                565                 570                 575

Pro Lys Ser Gln Trp Phe Cys Pro Pro Cys Leu Val Gly Thr Gly His
        580                 585                 590

Asp Phe Gly Phe Asp Asp Gly Glu Thr His Ser Leu Tyr Thr Phe Trp
    595                 600                 605

Gln Arg Ala Glu Ala Phe Lys Arg Asp Trp Trp Ser Lys His Gln Asp
610                 615                 620                 625

His Leu Trp Arg Pro Asp Ser Glu Gly Leu Ala Thr Ser Asp Tyr Asp
            630                 635                 640

Pro Pro Thr Asn Gly Leu Ala Arg Arg Val His Gly Thr Asp Leu Val
                645                 650                 655

Val Ser Glu Asp Asp Val Glu Arg Glu Phe Trp Arg Leu Val His Ser
        660                 665                 670

Gln Lys Glu Glu Val Glu Val Glu Tyr Gly Ala Asp Val His Ser Thr
    675                 680                 685

Thr His Gly Ser Ala Leu Pro Thr Gln Glu Thr His Pro Leu Ser Leu
690                 695                 700                 705

Tyr Ser Arg Asp Lys Trp Asn Leu Asn Asn Leu Pro Ile Leu Pro Gly
            710                 715                 720

Ser Leu Leu Gln Tyr Ile Lys Ser Asp Ile Ser Gly Met Thr Val Pro
                725                 730                 735

Trp Ile Tyr Val Gly Met Ile Phe Ser Thr Phe Cys Trp His Asn Glu
        740                 745                 750

Asp His Tyr Thr Tyr Ser Ile Asn Tyr Gln His Trp Gly Glu Thr Lys
    755                 760                 765

Thr Trp Tyr Gly Ile Pro Gly Glu Asp Ala Glu Lys Phe Glu Asn Ala
770                 775                 780                 785

Met Arg Lys Ala Ala Pro Asp Leu Phe Glu Thr Leu Pro Asp Leu Leu
            790                 795                 800

Phe His Leu Thr Thr Met Met Ser Pro Glu Lys Leu Lys Lys Glu Gly
                805                 810                 815

Val Arg Val Ala Cys Asp Gln Arg Ala Asn Glu Phe Val Val Thr
        820                 825                 830

Phe Pro Lys Ala Tyr His Ser Gly Phe Asn His Gly Leu Asn Leu Asn
    835                 840                 845

Glu Ala Val Asn Phe Ala Leu Pro Asp Trp Ile Phe Asp Asp Leu Glu
850                 855                 860                 865

Ser Val Arg Arg Tyr Gln Arg Phe Arg Lys Pro Ala Val Phe Ser His
            870                 875                 880

Asp Gln Leu Leu Ile Thr Val Ser Gln Gln Ser Gln Thr Ile Glu Thr
                885                 890                 895

Ala Val Trp Leu Glu Ala Ala Met Gln Glu Met Val Asp Arg Glu Ile
        900                 905                 910

Ala Lys Arg Asn Ala Leu Arg Glu Ile Ile Pro Asp Leu Lys Glu Glu
    915                 920                 925

Val Tyr Asp Glu Asp Val Ala Glu Ser His Tyr Ile Cys Ser His Cys
930                 935                 940                 945

Thr Leu Phe Ser Tyr Leu Gly Gln Leu Thr Ser Pro Lys Thr Asp Gly
```

-continued

```
                950                 955                 960
Val Ala Cys Leu Asp His Gly Phe Glu Val Cys Asn Ala Asp Ala Pro
            965                 970                 975
Val Lys Trp Thr Leu Lys Leu Arg Phe Ser Asp Gln Leu Arg Ser
            980                 985                 990
Ile Leu Ala Lys Val Cys Glu Arg Ala Ala Val Pro Arg Asn Trp Ile
            995                 1000                1005
Gln Arg Leu Lys Lys Thr Leu Ala Leu Gly Pro Thr Pro Leu Lys
1010                1015                1020                1025
Thr Leu Arg Ser Leu Leu His Glu Gly Glu Lys Ile Ala Phe Ser Leu
                1030                1035                1040
Glu Pro Leu Glu Asp Leu Arg Thr Phe Val Thr Cys Ala Asn Ser Trp
                1045                1050                1055
Val Glu Arg Ala Asn Val Phe Leu Met Arg Lys Leu His Lys Arg Arg
                1060                1065                1070
Gly Glu Pro Ala Ala Ala Pro Ala Gly Arg Arg Arg Ser Lys Gly
            1075                1080                1085
Gly Ala Val Ala Asp Asp Ser Phe Thr Arg Arg Gln Ser Leu Asp Ala
1090                1095                1100                1105
Ser Val Asp Asp Ala Glu Ser Thr Ser Asp Arg Ser Pro Glu Ala Leu
                1110                1115                1120
Tyr Ala Leu Ile Gly Glu Leu Asp Ser Leu His Phe Asp Ala Pro Glu
                1125                1130                1135
Ile Ala Ser Leu Arg Thr Met Ala Gln Glu Leu Glu Glu Phe Ile Gly
                1140                1145                1150
Arg Cys Asp Glu Val Leu Gln Gln Gly Asp Glu Thr Asn Leu Lys Asp
                1155                1160                1165
Cys Glu Ser Ile Leu Thr Leu Gly Ser Ser Leu Asn Val Asp Ala Pro
1170                1175                1180                1185
Gln Ile Lys Glu Leu Ser Asp Tyr Val Glu Arg Arg Lys Trp Ile Gln
                1190                1195                1200
Glu Val Thr Glu Ser Phe Asp Thr Tyr Leu Tyr Tyr His Glu Val Ala
                1205                1210                1215
Glu Leu Leu Asp Arg Ala Asp Ser Cys Gly Leu Gln Asp His Glu Leu
                1220                1225                1230
Arg Lys Asn Leu Glu Gln Arg Leu Glu Ala Gly Gln Arg Trp Thr Glu
                1235                1240                1245
Ser Ala Arg Glu Ala Leu Gly Gly Ser Gln Pro Ile Thr Ile Asp Val
1250                1255                1260                1265
Leu Gln Glu Leu Ser Glu Ser Ser Ala Asp Val Pro Val Leu Glu
                1270                1275                1280
Val Ala Gln Asp Val Thr Asp Ala Leu Ser Lys Ala Lys Glu Leu Gln
                1285                1290                1295
Lys Thr Ile Gln Thr Leu Tyr Lys Ala Leu Gln Thr Gly Ala His Gly
                1300                1305                1310
His Ser Ala Ala Asp Ala Asp Gly Asp Leu Ser Met Ile Ser Ile Ser
                1315                1320                1325
Glu Asn Gly Glu Ala Ala Glu Arg Val Ala Leu Leu Pro Asp Ala Arg
1330                1335                1340                1345
Arg Val Leu Arg Ala Ala Arg Ser Asn Lys Leu Glu Leu Glu His Ala
                1350                1355                1360
Gln Asp Ile Glu Lys Ala Val Gln Val Tyr Asp Ala Trp Arg Ala Ala
                1365                1370                1375
```

-continued

```
Phe Asn Gln Ile Met Gln Thr Ile Ala Gly Gly Ser Arg Arg Leu Thr
            1380                1385                1390

Asp Ala Asp Arg Asp Glu Glu Leu Asp Lys Leu Val Glu Arg Val Glu
    1395                1400                1405

Asp Ala Thr Asp Pro Ala Asp Asp Gln Asn Lys Pro Asn Ala Arg Asn
1410                1415                1420                1425

Cys Ile Cys Arg Ser Ser Met Pro Ile Ala Ile Pro Ser Ser Ser Gly
            1430                1435                1440

Ala Glu Cys Ser Arg Cys Arg Val Gln Tyr His Leu Ser Cys Ile Lys
            1445                1450                1455

Val Arg Ser Ser Glu Val Ser Arg Ala Glu Gly Gly Trp Val Cys Pro
            1460                1465                1470

Phe Cys Pro Trp Tyr Gly Ser Ala Pro Phe Leu Lys Met Arg Lys Ala
            1475                1480                1485

Ile Ser Ile Ala Asp Leu Ser Lys Leu Val Tyr Asp Gln Asp His Arg
1490                1495                1500                1505

Arg Asp Gln Phe Lys Phe Leu Pro Leu Glu Trp Asp Ala Ile Glu Glu
            1510                1515                1520

Val Val Ala Lys Ala Lys Arg Phe Glu Thr Ala Ala Lys Arg Met Ile
            1525                1530                1535

Lys Thr Leu Ser Leu Met Arg Arg Asp Gln Lys Gln Val Ile Leu Ala
            1540                1545                1550

His Trp Leu Arg Arg Ser Ile Gly Cys Pro Val Asp Val Leu Gly Pro
            1555                1560                1565

Glu Lys Val Asn Met Leu Asp Leu Ile Ser Glu Asn Leu Leu Ala Leu
1570                1575                1580                1585

Gly Ser Gln Gln Gly Asp Ala Ala Pro Met Ala Pro Val Glu Arg Ile
            1590                1595                1600

Lys Ala Ser Thr Pro Ala Arg Ser Asp Glu Arg Thr Glu Thr Thr
            1605                1610                1615

Pro Leu Pro Arg Ser Ser Arg Val Pro Ala Pro Ala Asp Arg Asp Ser
            1620                1625                1630

Gly Ser Pro Ala Val Arg Asp Asp Arg Lys Arg Lys Ala Lys Arg Gly
            1635                1640                1645

Lys Arg Ala Lys Leu Val Phe Gln Glu Glu Ile Gly Ile Gly Ala Tyr
1650                1655                1660                1665

Arg Asp Arg Gln Pro Ile Tyr Cys Leu Cys His Glu Pro Glu Ser Gly
            1670                1675                1680

Arg Met Ile Ala Cys Asp Lys Cys Met Leu Trp Phe His Thr Asn Cys
            1685                1690                1695

Val Arg Leu Asp Asp Pro Pro Asn Leu Gly Asn Glu Pro Trp Ile Cys
            1700                1705                1710

Pro Met Cys Cys Ile Lys Ala Glu Arg Lys Tyr Pro Gln Ala Glu Val
            1715                1720                1725

Arg Val Lys Asp Ile Gly Val Thr Asp Pro Asp Leu Trp Leu Asp Ile
1730                1735                1740                1745

Arg Ala Thr Leu Arg Ser Leu Glu Lys Pro Val Ser Lys Ile Gln Ser
            1750                1755                1760

Trp Thr Ser Pro Glu Asn Lys Arg Ile Val Leu His Leu Glu Lys Phe
            1765                1770                1775

Thr Pro Ala Ile His Ala Glu Glu Val His Ser Gln Ile Thr Lys Arg
            1780                1785                1790
```

-continued

```
Ala Arg Leu Glu Ser Asp Thr Pro Ser Lys Ala Arg Val Ser Leu Gly
    1795                1800                1805
Arg Ser Asp Ser Ile Ser Thr Pro Ala Lys Glu Ser Gly Ala Val Pro
1810                1815                1820                1825
Tyr Ala Ala Ala Pro Val Pro Ser Glu Ala Val Arg Gly Ile Val Pro
                1830                1835                1840
Ala Leu Thr Pro Ala Ala Asp Ser Pro Ala Ser Arg Ser Gly Arg Asn
            1845                1850                1855
Asp Asp Ser Phe Ala Ala Ser Pro Pro Leu Trp Asp Ala Lys Thr
        1860                1865                1870
Gly Pro Ser Pro Gly Asn Ala Ser Ile Glu Trp Ala Gln Ser Ala Arg
        1875                1880                1885
Arg Arg Tyr Ala Glu Gly Met Asp Asn Leu Tyr Arg Arg Gly Ile Thr
1890                1895                1900                1905
Asp Thr Met Leu Val Arg Phe Tyr Val Gly Trp Asn Gly Arg Thr Leu
                1910                1915                1920
Phe His Pro Val Arg Asp Ser Ala Gly Asn Ile Val Glu Val Ser Leu
            1925                1930                1935
Gly Glu Asn Val Arg Leu His Pro Asp Asp Pro Glu Gly Val Arg Val
            1940                1945                1950
Ile Arg Ala Ala Ile Glu Arg His Ser Val Lys Ala Asp Arg Leu Ala
        1955                1960                1965
Ala Ser His Gly Tyr Gly Gly Glu Met Asp Asp His Val Tyr Ser Arg
1970                1975                1980                1985
Asn Ala Tyr Ser Arg Asp Asp Gly Arg Tyr Thr Ala Gln Arg Arg Asp
                1990                1995                2000
Pro Pro Val Val Pro Ser Asn Gly Arg Phe Ser Met Arg Ser Pro Ala
            2005                2010                2015
Thr Ile Pro Ser Gln Arg Leu Gly Ser Asp Arg Asp Tyr Glu Arg Glu
            2020                2025                2030
Arg Glu Arg Asp Gly Asp Leu His Asp Ala Arg Asp Gly Arg Asp Gly
    2035                2040                2045
Arg Tyr Gly Asp Ser Leu Arg Ser Pro Ala Ala Pro Val Ala Ala Met
2050                2055                2060                2065
Thr Ala Pro Gly Ala Leu Asp Thr Ser Pro Ala Leu Arg Thr Asn Leu
                2070                2075                2080
Ala Arg Glu Val Val Pro Thr Tyr Ala Arg Ser Ser Ala Asn Ala Ser
            2085                2090                2095
Ala Thr Thr Ser Pro Tyr Thr Gly Ala Ala Ser Thr Tyr Ser Ile Tyr
            2100                2105                2110
Ser Ala Ser Asp Arg Ala Ala Ser Tyr Pro Val Gly Arg Ser Ser Ile
    2115                2120                2125
Ser Gln Ala Asp Leu Asp Gly Asn Arg Gly Pro Pro Met Ala
2130                2135                2140                2145
Met Tyr Ala Ser Ala Lys Ala Glu Pro Val Ala Asn Gly Ser Thr Phe
            2150                2155                2160
Ser Ala Leu Asp Pro Ala Met Met Ala Asp Ala Ala Gly Gln Ile
        2165                2170                2175
Asp Pro Asn Leu Thr Ser Ser Pro Val Leu Ala Ser Asn Ser Ala Val
            2180                2185                2190
Pro Ala Pro Ser Thr Ala Pro Ala Ala His Gly Val Arg Ser Glu
    2195                2200                2205
Thr Arg Ser Arg Pro Pro Ser Ala Gly Asn Glu Val Ala His Glu Ala
```

-continued

```
          2210                2215                2220                    2225
Gly Ser Ala Lys Ala Pro Pro Gly Ala Pro Ser Gly Gly His Ser Gly
                    2230                2235                2240

Glu Ile Lys Glu His Asn Pro Asp Glu His Glu Leu Glu Ser Val Arg
            2245                2250                2255

Gln Gln Ala Arg Gln Met Ala Arg Lys Met Arg Pro Asp Ala Ser Glu
        2260                2265                2270

Ala Asp Ile Glu Arg Leu Val Gln Asn Phe Ile Gly Gly Gly Glu Ser
    2275                2280                2285

Lys
```